United States Patent
Bardy

(10) Patent No.: US 8,702,603 B2
(45) Date of Patent: Apr. 22, 2014

(54) SYSTEM AND APPARATUS FOR PROVIDING BASELINE DATA FOR AUTOMATED PATIENT MANAGEMENT

(75) Inventor: Gust H. Bardy, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 325 days.

(21) Appl. No.: 11/635,364

(22) Filed: Dec. 6, 2006

(65) Prior Publication Data

US 2007/0179357 A1 Aug. 2, 2007

Related U.S. Application Data

(63) Continuation of application No. 11/102,522, filed on Apr. 8, 2005, now abandoned, which is a continuation of application No. 09/860,987, filed on May 18, 2001, now Pat. No. 6,945,934, which is a continuation of application No. 09/476,601, filed on Dec. 31, 1999, now Pat. No. 6,280,380, which is a continuation-in-part of application No. 09/361,332, filed on Jul. 26, 1999, now Pat. No. 6,221,011.

(51) Int. Cl.
   *A61B 5/00* (2006.01)
   *G06F 19/00* (2011.01)

(52) U.S. Cl.
   CPC ............ *A61B 5/0002* (2013.01); *G06F 19/322* (2013.01)
   USPC ....................................................... 600/300

(58) Field of Classification Search
   USPC ................... 600/300, 301; 128/903–905, 920
   See application file for complete search history.

(56) References Cited

U.S. PATENT DOCUMENTS

| | | |
|---|---|---|
| 3,837,339 A | 9/1974 | Aisenberg et al. |
| 4,142,533 A | 3/1979 | Brownlee et al. |
| 4,197,856 A | 4/1980 | Northrop |
| 4,428,378 A | 1/1984 | Anderson et al. |
| 4,531,527 A | 7/1985 | Reinhold, Jr. et al. |
| 4,566,461 A | 1/1986 | Lubell et al. |
| 4,686,999 A | 8/1987 | Snyder et al. |

(Continued)

FOREIGN PATENT DOCUMENTS

| | | |
|---|---|---|
| AU | 751467 | 8/2002 |
| AU | 759502 | 4/2003 |

(Continued)

OTHER PUBLICATIONS

Dunn et al., "Telemedicine Links Patients in Sioux Lookout with Doctors in Toronto," CMA Journal, vol. 122, pp. 484-487 (Feb. 23, 1980).

(Continued)

*Primary Examiner* — Bill Thomson
*Assistant Examiner* — Shirley Jian
(74) *Attorney, Agent, or Firm* — Pauly, DeVries, Smith & Deffner, LLC

(57) ABSTRACT

A system and method for providing baseline data for automated patient management is disclosed. A patient is identified for enrollment in automated patient management with information including at least one of treatment profile and medical history. Device measures are collected to provide raw physiometry for the patient regularly recorded by a medical device, beginning with an initial observation period. Derived device measures are determined to provide derivative physiometry based on the collected device measures. Baseline data from the collected and derived device measures are quantified.

13 Claims, 23 Drawing Sheets

(56) References Cited

U.S. PATENT DOCUMENTS

| | | |
|---|---|---|
| 4,803,625 A | 2/1989 | Fu et al. |
| 4,809,697 A | 3/1989 | Causey, III et al. |
| 4,852,570 A | 8/1989 | Levine |
| 4,899,758 A | 2/1990 | Finkelstein et al. |
| 4,958,645 A | 9/1990 | Cadell et al. |
| 4,974,607 A | 12/1990 | Miwa |
| 4,987,897 A | 1/1991 | Funke |
| 5,040,536 A | 8/1991 | Riff |
| 5,113,859 A | 5/1992 | Funke |
| 5,113,869 A | 5/1992 | Nappholz et al. |
| 5,133,346 A | 7/1992 | Kulkarni |
| 5,178,149 A | 1/1993 | Imburgia et al. |
| 5,199,428 A | 4/1993 | Obel et al. |
| 5,301,105 A | 4/1994 | Cummings, Jr. |
| 5,307,263 A | 4/1994 | Brown |
| 5,309,919 A | 5/1994 | Snell et al. |
| 5,313,593 A | 5/1994 | Barakat et al. |
| 5,331,549 A | 7/1994 | Crawford, Jr. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,464,012 A | 11/1995 | Falcone |
| 5,544,661 A | 8/1996 | Davis et al. |
| 5,553,609 A | 9/1996 | Chen et al. |
| 5,557,514 A | 9/1996 | Seare et al. |
| 5,576,952 A | 11/1996 | Stutman |
| 5,584,868 A | 12/1996 | Salo et al. |
| 5,591,215 A | 1/1997 | Greenhut et al. |
| 5,603,331 A | 2/1997 | Heemels et al. |
| 5,660,183 A | 8/1997 | Chiang et al. |
| 5,673,691 A * | 10/1997 | Abrams et al. ................. 600/300 |
| 5,687,734 A | 11/1997 | Dempsey et al. |
| 5,697,959 A | 12/1997 | Poore |
| 5,704,345 A | 1/1998 | Berthon-Jones |
| 5,704,366 A | 1/1998 | Tracklind et al. |
| 5,711,297 A | 1/1998 | Iliff |
| 5,712,580 A | 1/1998 | Baumgartner et al. |
| 5,713,350 A | 2/1998 | Yokota et al. |
| 5,719,908 A | 2/1998 | Greeff et al. |
| 5,720,770 A | 2/1998 | Nappholz et al. |
| 5,720,771 A | 2/1998 | Snell |
| 5,724,580 A | 3/1998 | Levin et al. |
| 5,724,983 A | 3/1998 | Selker et al. |
| 5,738,102 A | 4/1998 | Lemelson |
| 5,743,267 A | 4/1998 | Nikolic |
| 5,749,907 A * | 5/1998 | Mann ................. 607/27 |
| 5,752,976 A | 5/1998 | Duffin et al. |
| 5,769,074 A | 6/1998 | Barnhill et al. |
| 5,772,586 A | 6/1998 | Heinonen et al. |
| 5,772,599 A | 6/1998 | Nevo et al. |
| 5,772,604 A | 6/1998 | Langberg et al. |
| 5,778,882 A | 7/1998 | Raymond et al. |
| 5,785,650 A | 7/1998 | Akasaka et al. |
| 5,785,660 A | 7/1998 | Van Lake et al. |
| 5,788,640 A | 8/1998 | Peters |
| 5,788,643 A | 8/1998 | Feldman |
| 5,792,062 A | 8/1998 | Poon et al. |
| 5,819,251 A | 10/1998 | Kremer et al. |
| 5,855,593 A | 1/1999 | Olson et al. |
| 5,860,918 A | 1/1999 | Schradi et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,993,386 A | 11/1999 | Ericsson |
| 6,004,276 A | 12/1999 | Wright et al. |
| 6,014,581 A | 1/2000 | Whayne et al. |
| 6,024,699 A | 2/2000 | Surwit et al. |
| 6,038,469 A | 3/2000 | Karlsson et al. |
| 6,047,203 A | 4/2000 | Sackner et al. |
| 6,050,940 A | 4/2000 | Braun |
| 6,053,866 A * | 4/2000 | McLeod ................. 600/300 |
| 6,063,028 A | 5/2000 | Luciano |
| 6,067,466 A | 5/2000 | Selker |
| 6,073,046 A | 6/2000 | Patel |
| 6,080,106 A * | 6/2000 | Lloyd et al. ................. 600/300 |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,122,351 A | 9/2000 | Schlueter, Jr. et al. |
| 6,129,675 A | 10/2000 | Jay |
| 6,135,951 A | 10/2000 | Richardson et al. |
| 6,139,494 A | 10/2000 | Cairnes |
| 6,152,882 A | 11/2000 | Prutchi |
| 6,155,267 A | 12/2000 | Nelson |
| 6,166,563 A | 12/2000 | Volk et al. |
| 6,168,563 B1 | 1/2001 | Brown |
| 6,168,653 B1 | 1/2001 | Myers |
| 6,171,237 B1 | 1/2001 | Avitall et al. |
| 6,171,256 B1 | 1/2001 | Joo et al. |
| 6,203,495 B1 | 3/2001 | Bardy |
| 6,211,011 B1 | 4/2001 | Chen |
| 6,221,011 B1 | 4/2001 | Bardy |
| 6,223,078 B1 | 4/2001 | Marcovecchio |
| 6,225,901 B1 | 5/2001 | Kail, IV |
| 6,234,964 B1 | 5/2001 | Iliff |
| 6,246,992 B1 | 6/2001 | Brown |
| 6,248,080 B1 | 6/2001 | Miesel et al. |
| 6,249,705 B1 | 6/2001 | Snell |
| 6,250,309 B1 | 6/2001 | Krichen et al. |
| 6,261,230 B1 | 7/2001 | Bardy |
| 6,263,245 B1 | 7/2001 | Snell |
| 6,270,457 B1 | 8/2001 | Bardy |
| 6,277,072 B1 | 8/2001 | Bardy |
| 6,280,380 B1 | 8/2001 | Bardy |
| 6,283,923 B1 | 9/2001 | Finkelstein et al. |
| 6,287,252 B1 | 9/2001 | Lugo |
| 6,290,646 B1 | 9/2001 | Cosentino et al. |
| 6,302,844 B1 | 10/2001 | Walker |
| 6,306,088 B1 | 10/2001 | Krausman et al. |
| 6,312,378 B1 | 11/2001 | Bardy |
| 6,331,160 B1 | 12/2001 | Bardy |
| 6,336,900 B1 | 1/2002 | Alleckson |
| 6,336,903 B1 | 1/2002 | Bardy |
| 6,338,039 B1 * | 1/2002 | Lonski et al. ................. 705/3 |
| 6,361,501 B1 * | 3/2002 | Amano et al. ................. 600/500 |
| 6,363,282 B1 | 3/2002 | Nichols et al. |
| 6,368,284 B1 | 4/2002 | Bardy |
| 6,379,301 B1 | 4/2002 | Worthington et al. |
| 6,398,728 B1 | 6/2002 | Bardy |
| 6,411,840 B1 | 6/2002 | Bardy |
| 6,416,471 B1 | 7/2002 | Kumar et al. |
| 6,428,483 B1 | 8/2002 | Carlebach |
| 6,440,066 B1 | 8/2002 | Bardy |
| 6,442,432 B2 | 8/2002 | Lee et al. |
| 6,442,433 B1 | 8/2002 | Linberg |
| 6,454,705 B1 | 9/2002 | Cosentino et al. |
| 6,454,707 B1 | 9/2002 | Casscells, III et al. |
| 6,473,646 B2 | 10/2002 | Sun et al. |
| 6,477,424 B1 | 11/2002 | Thompson et al. |
| 6,478,737 B2 | 11/2002 | Bardy |
| 6,480,745 B2 | 11/2002 | Nelson et al. |
| 6,497,655 B1 | 12/2002 | Linberg et al. |
| 6,512,949 B1 | 1/2003 | Combs et al. |
| 6,524,239 B1 * | 2/2003 | Reed et al. ................. 600/300 |
| 6,564,104 B2 | 5/2003 | Nelson et al. |
| 6,648,820 B1 | 11/2003 | Sarel |
| 6,662,032 B1 | 12/2003 | Gavish et al. |
| 6,804,656 B1 * | 10/2004 | Rosenfeld et al. ................. 705/3 |
| 6,811,537 B2 | 11/2004 | Bardy |
| 6,827,670 B1 | 12/2004 | Stark et al. |
| 6,866,629 B2 | 3/2005 | Bardy |

(56) References Cited

U.S. PATENT DOCUMENTS

| | | | |
|---|---|---|---|
| 6,887,201 | B2 | 5/2005 | Bardy |
| 6,893,397 | B2 | 5/2005 | Bardy |
| 6,908,437 | B2 | 6/2005 | Bardy |
| 6,920,360 | B2 | 7/2005 | Lee et al. |
| 6,945,494 | B2 | 9/2005 | Bagnall |
| 6,945,934 | B2 | 9/2005 | Bardy |
| 6,960,167 | B2 | 11/2005 | Bardy |
| 7,104,955 | B2 | 9/2006 | Bardy |
| 7,134,996 | B2 | 11/2006 | Bardy |
| 7,147,600 | B2 | 12/2006 | Bardy |
| 7,248,916 | B2 | 7/2007 | Bardy |
| 7,837,629 | B2 | 11/2010 | Bardy |
| 7,874,993 | B2 | 1/2011 | Bardy |
| 7,972,274 | B2 | 7/2011 | Bardy |
| 2001/0023360 | A1 | 9/2001 | Nelson et al. |
| 2001/0039375 | A1 | 11/2001 | Lee et al. |
| 2003/0055679 | A1 | 3/2003 | Soll et al. |
| 2004/0122486 | A1 | 6/2004 | Stahmann et al. |
| 2007/0293741 | A1 | 12/2007 | Bardy |
| 2011/0046493 | A1 | 2/2011 | Bardy |
| 2011/0172548 | A1 | 7/2011 | Bardy |
| 2011/0224563 | A1 | 9/2011 | Bardy |

FOREIGN PATENT DOCUMENTS

| | | |
|---|---|---|
| AU | 759934 | 5/2003 |
| CA | 2314517 | 1/2001 |
| EP | 0 34 2859 | 11/1989 |
| EP | 0 513 457 | 11/1992 |
| EP | 0 531 889 A2 | 3/1993 |
| EP | 0 711 531 A1 | 5/1996 |
| EP | 0887759 | 12/1998 |
| EP | 1057448 | 12/2000 |
| EP | 1102196 | 5/2001 |
| EP | 1102199 | 5/2001 |
| EP | 1107158 | 3/2008 |
| WO | WO 97/39792 | 10/1997 |
| WO | WO 98/01742 | 2/1998 |
| WO | WO-9807142 | 2/1998 |
| WO | WO 98/42103 | 9/1998 |
| WO | WO-99/14882 | 3/1999 |
| WO | WO 99/46718 | 9/1999 |
| WO | WO 99/55226 | 11/1999 |
| WO | WO-99/55226 | 11/1999 |
| WO | WO-03027936 | 4/2003 |

OTHER PUBLICATIONS

Auer et al., "Paced Epimyocardial Electrograms for Noninvasive Rejection Monitoring After Heart Transplantation," The Journal of Heart and Lung Transplantation, vol. 15, No. 10, pp. 993-998 (Oct. 1996).

Schreier et al., "A Non-Invasive Rejection Monitoring System Based on Remote Analysis of Intramyocardial Electrograms from Heart Transplants," IEEE, pp. 35-36 (1997).

Roberge et al., "Basic and Applied Biomedical Engineering Building Blocks for Health Care," 1995 IEEE Engineering in Medicine and Biology 17th Annual Conference, vol. 1, Montreal-Canada, (Sep. 20-23, 1995).

Hutten et al., "Cardiac Telemonitoring by Integrating Pacemaker Telemetry within Worldwide Data Communication Systems," Proceedings of 19th International Conference, IEEE/EMBS, Chicago, IL, pp. 974-976 (Oct. 30-Nov. 2, 1997).

Vargas, Juan E., "Home-Based Monitoring of Cardiac Patients," Dept. of Electr. & Comput. Eng., South Carolina Univ., Columbia, SC, Information Technology Applications in Biomedicine, Proceedings., 1998 IEEE International Conference, pp. 133-136 (May 16-17, 1998).

Magrabi et al., "Web Based Longitudinal ECG Monitoring," Proceedings of 20th Annual International Conference of the IEEE Engineering in Medicine and Biology Society, vol. 20, No. 3, pp. 1155-1158 (1998).

Nelwan et al., "Ubiquitous Access to Real-Time Patient Monitoring Data," Computers in Cardiology., vol. 24, pp. 271-274 (1997).

Moody GB, "Integration of Real-Time and Off-Line Clinical Data in the MIMIC Database," Computers in Cardiology 1997 vol. 24, pp. 585-588, Cambridge, MA USA.

Long WJ, et al., "Differential Diagnosis Generation From a Causal Network With Probabilities," Computers in Cardiology, 1988, Proceedings, pp. 185-188, Washington DC, USA Braunwald, "Heart Disease: A Textbook of Cardiovascular Medicine" 5th Ed., W.B. Saunders Co., vol. 1, pp. 451-455 (1997).

File History for U.S. Appl. No. 11/880,754, filed Jul. 23, 2007, 26 pgs. (downloaded from USPTO website).

File History for U.S. Appl. No. 11/102,522, filed Apr. 8, 2005, 200 pgs. (downloaded from USPTO website).

Discovery® II Pacemaker System Guide Manual, Dec. 2003 (207 pages).

Discoverytm II Pacemaker Physician's Technical Manual, Oct. 1999 (6 pages).

EP Search Report for EP Patent Application No. 00202604.05, dated Dec. 8, 2000, which corresponds to U.S. Appl. No. 09/361,332, which is the parent application to the present application (U.S. Appl. No. 11/635,364) (2 pages).

Medtronic GEM® 7227Cx, 7227B, 7227D, 7227E Implantable Cardioverter Defibrillators, Sep. 2001 (313 pages).

Medtronic GEM® II DR 7273 Dual Chamber Implantable Cardioverter Defibrillator 9964E Software, Jan. 2001 (402 pages).

Office Actions and Responses for U.S. Appl. No. 11/635,205, filed Dec. 6, 2006 (41 pages).

Operators Manual for the Model 2901 Portable Programmer Recorder Monitor by Guidant, Jan. 1999 (22 pages).

Office Actions, Responses and Allowance-related documents for EP Patent Application No. 00202604.05, filed Jul. 20, 2000, which corresponds to U.S. Appl. No. 09/361,332, which is the parent application to the present application (U.S. Appl. No. 11/635,364) (40 pages).

Belardinelli et al., "A Four-Minutes Submaximal Constant Work Rate Exercise Test to Assess Cardiovascular Functional Class in Chronic Heart Failure", The American Journal of Cardiology, 81:1210-1214 (1998).

File History (as of Jul. 22, 2010) for co-pending U.S. Appl. No. 10/876,118, filed Jun. 24, 2004, "System and Method for Analyzing a Patient Status for Congestive Heart Failure for Use in Automated Patient" (377 pages).

File History (as of Jul. 22, 2010) for co-pending U.S. Appl. No. 11/150,334, filed Jun. 10, 2005, entitled "System and Method for Diagnosing and Monitoring Congestive Heart Failure" (298 pages).

File History (as of Jul. 22, 2010) for co-pending U.S. Appl. No. 11/635,205, filed Dec. 6, 2006, entitled "System and Method for Generating Baseline Data for Automated Management of Edema", which claims priority to the same parent application (U.S. Appl. No. 09/361,332) as the present application (U.S. Appl. No. 11/635,365) (279 pages).

File History (as of Jul. 22, 2010) for co-pending U.S. Appl. No. 11/894,514, filed Aug. 20, 2007 which is abandoned, entitled "System and Method for Determining a Reference Baseline for Use in Heart Failure Assessment", which claims priority to the same parent application (U.S. Appl. No. 09/361,332) as the present application (U.S. Appl. No. 11/635,365) (232 pages).

Office Actions, Responses and Appeal-related documents for EP Patent Application No. 00650193, filed Nov. 16, 2000, which corresponds to U.S. Appl. No. 09/441,623, filed Nov. 16, 1999 (113 pages).

EP Search Report dated Apr. 2, 2002 for EP Patent Application No. 00650193.6, filed Nov. 16, 2000, which corresponds to U.S. Appl. No. 09/441,623, filed Nov. 16, 1999 (4 pages).

Examiner's First Report dated Jun. 22, 2005 for AU Patent Application No. 2002302016, which corresponds to U.S. Appl. No. 09/441,623, filed Nov. 16, 1999 (2 pages).

File History for Canadian Patent Application No. 2325660 (abandoned) which corresponds to U.S. Appl. No. 09/441,623, filed Nov. 16, 1999 (17 pages).

Partial File History (from Jul. 23, 2010 to Feb. 7, 2011) for co-pending U.S. Appl. No. 10/876,118, filed Jun. 24, 2004, "System and

(56) References Cited

OTHER PUBLICATIONS

Method for Analyzing a Patient Status for Congestive Heart Failure for Use in Automated Patient", which is a parent application to the present U.S. Appl. No. 11/150,334 (80 pages).

Partial File History (from Jul. 23, 2010 to Feb. 7, 2011) for co-pending U.S. Appl. No. 11/894,514, filed Dec. 6, 2006, entitled "System and Method for Providing Baseline Data for Automated Patient Management", which claims priority to the same parent application (U.S. Appl. No. 09/361,332) as the present application (U.S. Appl. No. 11/894,514) (47 pages).

Partial File History (from Feb. 8, 2011 through Jun. 2, 2011) for co-pending U.S. Appl. No. 10/876,118, filed Jun. 24, 2004, "System and Method for Analyzing a Patient Status for Congestive Heart Failure for Use in Automated Patient" (43 pages).

File History (as of Jun. 2, 2011) for co-pending U.S. Appl. No. 13/073,301, filed Mar. 28, 2011, "System and Method for Diagnosing and Monitoring Congestive Heart Failure" (96 pages).

File History (as of Jun. 2, 2011) for co-pending U.S. Appl. No. 13/115,266, filed May 25, 2011, "System and Method for Analyzing a Patient Status for Congestive Heart Failure for Use in Automated Patient" (91 pages).

File History (as of Jun. 2, 2011) for co-pending U.S. Appl. No. 12/938,686, filed Nov. 3, 2010, entitled "System and Method for Generating Baseline Data for Automated Management of Cardiovascular Pressure" (174 pages).

Partial File History (from Feb. 8, 2011 through Jun. 2, 2011) for co-pending U.S. Appl. No. 11/894,514, filed Dec. 6, 2006, entitled "System and Method for Providing Baseline Data for Automated Patient Management", which claims priority to the same parent application (U.S. Appl. No. 09/361,332) as the present application (U.S. Appl. No. 11/635,364) (62 pages).

Van Bemmel, J. H. et al., "Handbook of Medical Informatics", Handbook of Medical Informatics, 1997, 8: pp. 117-125.

Degoulet, Patrice et al., "Introduction to Clinical Informatics", Computers in Heath Care, 1996, 10: pp. 131-138.

Uckun, Serdar, "Intelligent systems in patient monitoring and therapy management", International Journal of Clinical Monitoring and Computing, 1994, 11: pp. 241-253.

Dawant, Benoit M. et al., "SIMON: A Distributed Computer Architecture for Intelligent Patient Monitoring", Expert Systems With Applications, 1993, vol. 6, pp. 411-420.

Puers, B. et al., "Patient Monitoring Systems", IEEE, 1989, pp. 1-6.

Nelson, Charlotte L. et al., "Relation of Clinical and Angiographic Factors to Functional Capacity as Measured by the Duke Activity Status Index", The American Journal of Cardiology, Oct. 1, 1991, vol. 68, pp. 973-975.

"File History of Office Actions and Responses for co-owned EP patent No. 1107158", From Dec. 21, 2000 to Feb. 28, 2008, Entitled "System and Method for Determining a Reference Baseline for Individual Patient Status for Use in an Automated Collection and Analysis Patient Care System," (510 pages).

Benditt, DG et al., "Single-chamber cardiac pacing with activity-initiated chronotropic response: evaluation by cardiopulmonary exercise testing", Circulation, 1987, 75: 184-191.

"Non-Final Office Action", from U.S. Appl. No. 11/894,514, mailed Jun. 18, 2013, 11 pages.

\* cited by examiner

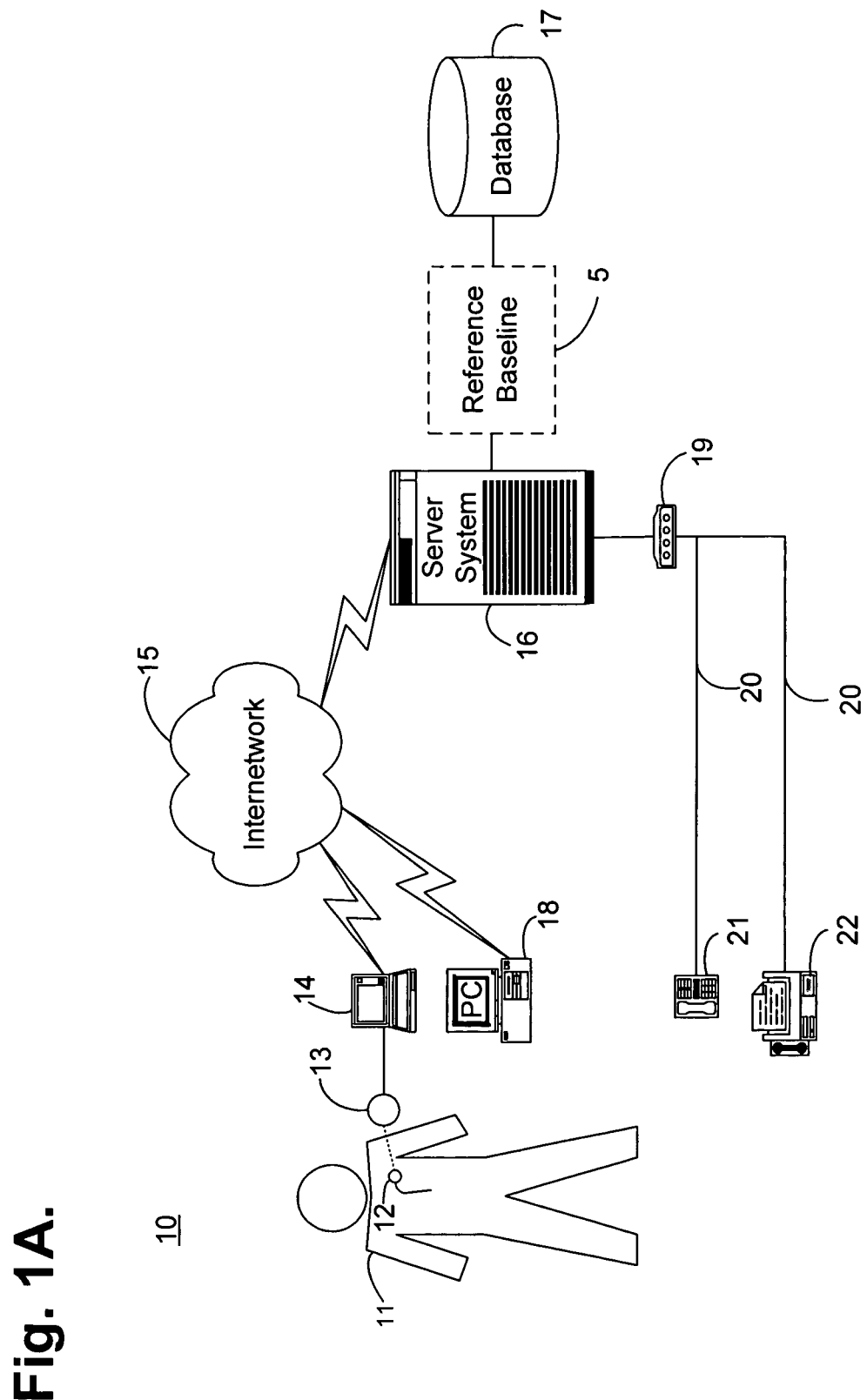

Fig. 6. 110

| 111 | 112 | 113 | 114 | 115 | ... | 116 |
|---|---|---|---|---|---|---|
| Health Wellness | Shortness of Breath | Energy Level | Exercise Tolerance | Chest Discomfort | | Time of Day |

Fig. 7. 120

| 121 | 122 | 123 | 124 | 125 | 126 | 127 | 128 | 129 | 130 | 131 |
|---|---|---|---|---|---|---|---|---|---|---|
| Atrial Electrical Activity | Ventricular Electrical Activity | Minute Ventilation | Patient Activity Score | Cardiac Output Score | Mixed Venous Oxygenation Score | Pulmonary Artery Diastolic Pressure Measure | Time of Day | Interventions Made | Success of Interventions Made | Battery Status and Program Settings |

Fig. 15.

SYSTEM AND APPARATUS FOR PROVIDING BASELINE DATA FOR AUTOMATED PATIENT MANAGEMENT

CROSS-REFERENCE TO RELATED APPLICATION

This Patent application is a continuation of U.S. patent application Ser. No. 11/102,522, filed on Apr. 8, 2005, abandoned, which is a continuation of U.S. application Ser. No. 09/860,987, U.S. Pat. No. 6,945,934, issued Sep. 20, 2005, which is a continuation of U.S. application Ser. No. 09/476,601, U.S. Pat. No. 6,280,380, issued Aug. 28, 2001, which is a continuation-in-part of U.S. application Ser. No. 09/361,332, U.S. Pat. No. 6,221,011, issued Apr. 24, 2001, the priority of filing dates of which are claimed, and the disclosures of which are incorporated by reference.

FIELD OF THE INVENTION

The present invention relates in general to automated data collection and analysis, and, in particular, to a system and method for determining a reference baseline record for use in automated patient care.

BACKGROUND OF THE INVENTION

A broad class of medical subspecialties, including cardiology, endocrinology, hematology, neurology, gastroenterology, urology, ophthalmology, and otolaryngology, to name a few, rely on accurate and timely patient information for use in aiding health care providers in diagnosing and treating diseases and disorders. Often, proper medical diagnosis requires information on physiological events of short duration and sudden onset, yet these types of events are often occur infrequently and with little or no warning. Fortunately, such patient information can be obtained via external, implantable, cutaneous, subcutaneous, and manual medical devices, and combinations thereof. For example, in the area of cardiology, implantable pulse generators (IPGs) are medical devices commonly used to treat irregular heartbeats, known as arrhythmias. There are three basic types of IPGs. Cardiac pacemakers are used to manage bradycardia, an abnormally slow or irregular heartbeat. Bradycardia can cause symptoms such as fatigue, dizziness, and fainting. Implantable cardioverter defibrillators (ICDs) are used to treat tachycardia, heart rhythms that are abnormally fast and life threatening. Tachycardia can result in sudden cardiac death (SCD). Finally, implantable cardiovascular monitors and therapeutic devices are used to monitor and treat structural problems of the heart, such as congestive heart failure, as well as rhythm problems.

Pacemakers and ICDs, as well as other types of implantable and external medical devices, are equipped with an on-board, volatile memory in which telemetered signals can be stored for later retrieval and analysis. In addition, a growing class of cardiac medical devices, including implantable heart failure monitors, implantable event monitors, cardiovascular monitors, and therapy devices, are being used to provide similar stored device information. These devices are able to store more than thirty minutes of per heartbeat data. Typically, the telemetered signals can provide patient device information recorded on a per heartbeat, binned average basis, or derived basis from, for example, atrial electrical activity, ventricular electrical activity, minute ventilation, patient activity score, cardiac output score, mixed venous oxygen score, cardiovascular pressure measures, time of day, and any interventions and the relative success of such interventions. In addition, many such devices can have multiple sensors, or several devices can work together, for monitoring different sites within a patient's body.

These telemetered signals can be remotely collected and analyzed using an automated patient care system. One such system is described in U.S. Pat. No. 6,312,378. The telemetered signals are recorded by an implantable medical device, such as an IPG or monitor, and periodically retrieved using an interrogator, programmer, telemetered signals transceiver, or similar device, for subsequent download. The downloaded telemetered signals are received by a network server on a regular, e.g., daily, basis as sets of collected measures which are stored along with other patient records in a database. The information is analyzed in an automated fashion and feedback, which includes a patient status indicator, is provided to the patient.

While such a system can serve as a valuable tool in automated, remote patient care, the accuracy of the patient care, particularly during the first few weeks of care, and the quality of the feedback provided to the patient would benefit from being normalized to a reference baseline of patient wellness. In particular, a starting point needs to be established for each individual patient for use in any such system in which medical device information, such as telemetered signals from implantable and external medical devices, is continuously monitored, collected, and analyzed. The starting point could serve as a reference baseline indicating overall patient status and wellness from the outset of remote patient care.

In addition, automated remote patient care poses a further challenge vis-à-vis evaluating quality of life issues. Unlike in a traditional clinical setting, physicians participating in providing remote patient care are not able to interact with their patients in person. Consequently, quality of life measures, such as how the patient subjectively looks and feels, whether the patient has shortness of breath, can work, can sleep, is depressed, is sexually active, can perform activities of daily life, and so on, cannot be implicitly gathered and evaluated.

Reference baseline health assessments are widely used in conventional patient health care monitoring services. Typically, a patient's vital signs, consisting of heart rate, blood pressure, weight, and blood sugar level, are measured both at the outset of care and periodically throughout the period of service. However, these measures are limited in their usefulness and do not provide the scope of detailed medical information made available through implantable and external medical devices. Moreover, such measures are generally obtained through manual means and do not ordinarily directly tie into quality of life assessments. Further, a significant amount of time generally passes between the collection of sets of these measures.

In addition, the uses of multiple sensors situated within a patient's body at multiple sites are disclosed in U.S. Pat. Nos. 5,040,536 ('536) and 5,987,352 ('352). In the '536 patent, an intravascular pressure posture detector includes at least two pressure sensors implanted in different places in the cardiovascular system, such that differences in pressure with changes in posture are differentially measurable. However, the physiological measurements are used locally within the device, or in conjunction with any implantable device, to effect a therapeutic treatment. In the '352 patent, an event monitor can include additional sensors for monitoring and recording physiological signals during arrhythmia and syncopal events. The recorded signals can be used for diagnosis, research or therapeutic study, although no systematic approach to analyzing these signals, particularly with respect to peer and general population groups, is presented.

Thus, there is a need for an approach to determining a meaningful reference baseline of individual patient status for use in a system and method for providing automated, remote patient care through the continuous monitoring and analysis of patient information retrieved from an implantable medical device. Preferably, such an approach would establish the reference baseline through initially received measures or after a reasonable period of observation. The reference baseline could be tied to the completion of a set of prescribed physical stressors. Periodic reassessments should be obtainable as necessary. Moreover, the reference baseline should preferably be capable of correlation to quality of life assessments.

There is a further need for an approach to monitoring patient wellness based on a reference baseline for use in an automated patient care system. Preferably, such an approach would dynamically determine whether the patient is trending into an area of potential medical concern, including indicating disease onset, progression, regression, and status quo.

There is a further need for an approach to determining a situation in which remote patient care is inappropriate based on a reference baseline of patient wellness. Preferably, such an approach would include a range of acceptance parameters as part of the reference baseline, thereby enabling those potential patients whose reference baseline falls outside those acceptance parameters to be identified.

SUMMARY OF THE INVENTION

The present invention provides a system and method for providing baseline data for automated patient management. The patient device information relates to individual measures recorded by and retrieved from implantable medical devices, such as IPGs and monitors. The patient device information is received on a regular, e.g., daily, basis as sets of collected measures, which are stored along with other patient records in a database. The information can be analyzed in an automated fashion and feedback provided to the patient at any time and in any location.

An embodiment is a system and method for providing baseline data for automated patient management. A patient is identified for enrollment in automated patient management with information including at least one of treatment profile and medical history. Device measures are collected to provide raw physiometry for the patient regularly recorded by a medical device, beginning with an initial observation period. Derived device measures are determined to provide derivative physiometry based on the collected device measures. Baseline data from the collected and derived device measures are quantified.

The present invention provides a meaningful, quantitative measure of patient wellness for use as a reference baseline in an automated system and method for continuous, remote patient care. The reference baseline increases the accuracy of remote patient care, particularly during the first few weeks of care, by providing a grounded starting assessment of the patient's health and well-being.

A collateral benefit of the reference baseline is the removal of physician "bias" which can occur when the apparent normal outward appearance of a patient belies an underlying condition that potentially requires medical attention. The reference baseline serves to objectify a patient's self-assessment of wellness.

The present invention also provides an objective approach to humanizing the raw measures recorded by medical devices, including implantable medical devices. Using known quality of life assessment instruments, a patient can be evaluated and scored for relative quality of life at a given point in time. The reference baseline of the present invention provides a means for correlating the quality of life assessment to machine-recorded measures, thereby assisting a physician in furthering patient care.

Finally, the present invention improves the chronicling of legal responsibility in patient care. A prescribed course of treatment can be traced back to a grounded point in time memorialized by the reference baseline. Thus, a medical audit trail can be generated with a higher degree of accuracy and certainty based on having an established originating point of reference.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIGS. 1A and 1B are block diagrams showing a system for determining a reference baseline of individual patient status for use in an automated collection and analysis patient care system in accordance with the present invention;

FIG. 6 is a database schema showing, by way of example, the organization of a reference baseline quality of life record for cardiac patient care stored as part of a patient care record in the database of the system of FIG. 1A;

FIG. 7 is a database schema showing, by way of example, the organization of a monitoring record for cardiac patient care stored as part of a patient care record in the database of the system of FIG. 1A;

FIG. 15 is a record view showing, by way of example, a set of partial cardiac patient care records stored in the database of the system of FIGS. 12A and 12B;

DETAILED DESCRIPTION

Figure 1B:
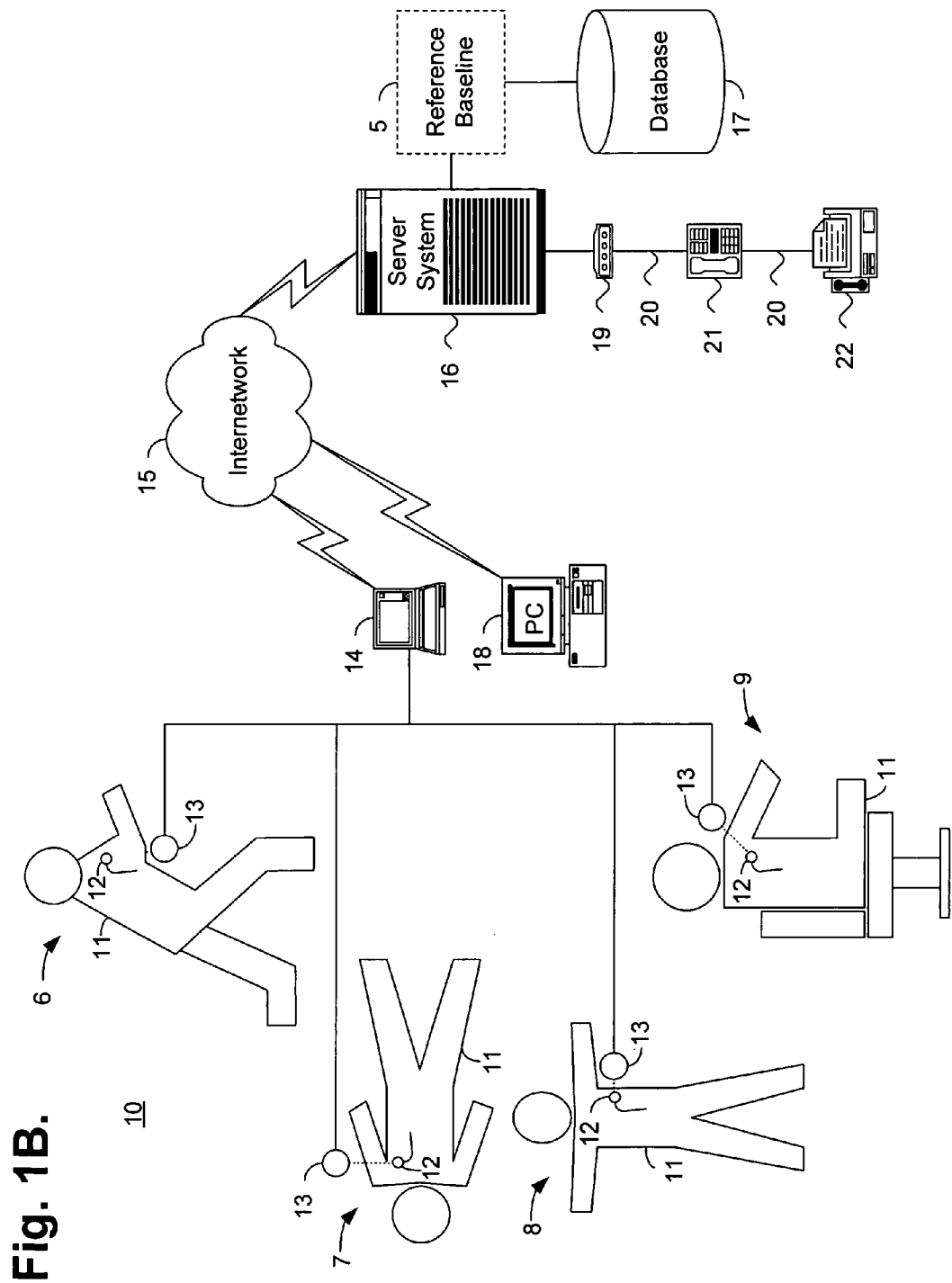

FIG. 1A is a block diagram showing a system 10 for determining a reference baseline 5 of patient status for an individual patient 11 for use in an automated collection and analysis patient care system in accordance with the present invention. An automated collection and analysis patient care system suitable for use with the present invention is disclosed in U.S. Pat. No. 6,312,378, the disclosure of which is incorporated herein by reference. A patient 11 is a recipient of an implantable medical device 12, such as, by way of example, an IPG or a heart failure or event monitor, with a set of leads extending into his or her heart. Alternatively, subcutaneous monitors or devices inserted into other organs (not shown) without leads could also be used. The implantable medical device 12 includes circuitry for recording into a short-term, volatile memory telemetered signals, which are stored as a set of collected measures for later retrieval.

For an exemplary cardiac implantable medical device, the telemetered signals non-exclusively present patient information recorded on a per heartbeat, binned average or derived basis and relating to: atrial electrical activity, ventricular electrical activity, minute ventilation, patient activity score, cardiac output score, mixed venous oxygenation score, cardiovascular pressure measures, time of day, the number and types of interventions made, and the relative success of any interventions, plus the status of the batteries and programmed settings. Examples of pacemakers suitable for use in the present invention include the Discovery line of pacemakers, manufactured by Guidant Corporation, Indianapolis, Ind. Examples of ICDs suitable for use in the present invention include the Gem line of ICDs, manufactured by Medtronic Corporation, Minneapolis, Minn.

In the described embodiment, the patient 11 has a cardiac implantable medical device. However, a wide range of related implantable medical devices are used in other areas of medicine and a growing number of these devices are also capable of measuring and recording patient information for later retrieval. These implantable medical devices include monitoring and therapeutic devices for use in metabolism, endocrinology, hematology, neurology, muscular disorders, gastroenterology, urology, ophthalmology, otolaryngology, orthopedics, and similar medical subspecialties. One skilled in the art would readily recognize the applicability of the present invention to these related implantable medical devices.

The telemetered signals stored in the implantable medical device 12 are retrieved upon completion of an initial observation period and subsequently retrieved on a continuous, periodic basis. By way of example, a programmer 14 can be used to retrieve the telemetered signals. However, any form of programmer, interrogator, recorder, monitor, or telemetered signals transceiver suitable for communicating with an implantable medical device 12 could be used, as is known in the art. In addition, a personal computer or digital data processor could be interfaced to the implantable medical device 12, either directly or via a telemetered signals transceiver configured to communicate with the implantable medical device 12.

Using the programmer 14, a magnetized reed switch (not shown) within the implantable medical device 12 closes in response to the placement of a wand 14 over the location of the implantable medical device 12. The programmer 14 communicates with the implantable medical device 12 via RF signals exchanged through the wand 14. Programming or interrogating instructions are sent to the implantable medical device 12 and the stored telemetered signals are downloaded into the programmer 14. Once downloaded, the telemetered signals are sent via an internetwork 15, such as the Internet, to a server system 16 which periodically receives and stores the telemetered signals in a database 17, as further described below with reference to FIG. 2.

An example of a programmer 14 suitable for use in the present invention is the Model 2901 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device to the internetwork 15, as is known in the art.

Other alternate telemetered signals transfer means could also be employed. For instance, the stored telemetered signals could be retrieved from the implantable medical device 12 and electronically transferred to the internetwork 15 using the combination of a remote external programmer and analyzer and a remote telephonic communicator, such as described in U.S. Pat. No. 5,113,869, the disclosure of which is incorporated herein by reference. Similarly, the stored telemetered signals could be retrieved and remotely downloaded to the server system 16 using a world-wide patient location and data telemetry system, such as described in U.S. Pat. No. 5,752, 976, the disclosure of which is incorporated herein by reference.

The initial set of telemetered signals recorded during the initial observation period is processed by the server system 16 into a set of reference measures and stored as a reference baseline 5 in the database 17, as further described below with reference to FIG. 3. The purpose of the observation period is to establish a reference baseline 5 containing a set of reference measures that can include both measured and derived patient information. The reference baseline 5 can link "hard" machine-recorded data with "soft" patient-provided self-assessment data from which can be generated a wellness status indicator. In addition, the reference baseline 5 can be used to identify patients for whom remote patient care may be inappropriate and for patient wellness comparison and analysis during subsequent, on-going remote patient care. The reference baseline 5 is maintained in the database 17 and can be reassessed as needed or on a periodic basis.

Subsequent to the initial observation period, the patient is remotely monitored by the server system 16 through the periodic receipt of telemetered signals from the implantable medical device 12 via the internetwork 15. Feedback is then provided back to the patient 11 through a variety of means. By way of example, the feedback can be sent as an electronic mail message generated automatically by the server system 16 for transmission over the internetwork 15. The electronic mail message is received by personal computer 18 (PC) situated for local access by the patient 11. Alternatively, the feedback can be sent through a telephone interface device 19 as an automated voice mail message to a telephone 21 or as an automated facsimile message to a facsimile machine 22, both also situated for local access by the patient 11. In addition to a personal computer 18, telephone 21, and facsimile machine 22, feedback could be sent to other related devices, including a network computer, wireless computer, personal data assistant, television, or digital data processor.

FIG. 1B is a block diagram showing a further embodiment of the present invention in which the patient 11 is monitored by the implantable medical device 12 while engaged in performing a prescribed set of timed physical stressors during an initial observation period or during a subsequent observation period if the patient 11 is being reassessed. The stressors are a set of normal, patient activities and cardiovascular and respiratory maneuvers that allow consistent, reproducible physiological functions to be measured by the implantable medical device 12. These maneuvers include activities such as a change in posture, simple physical exercises, breathing state, including holding breath and hyperventilating, and oxygen challenges. By way of example, the stressors include timed physical activities such as running in place 6, recumbency 7, standing 8, sitting motionless 9, and reprogramming at least one of pacing interventions and pacing modes of the implantable medical device 12, as further described below with reference to FIG. 5.

In a still further embodiment of the present invention, at least one of pacing interventions and pacing modes of the implantable medical device 12 is reprogrammed by the programmer 14 during the initial observation period or during a subsequent observation period if the patient 11 is being reassessed. The patient 11 is then monitored by the reprogrammed implantable medical device 12.

Figure 2:
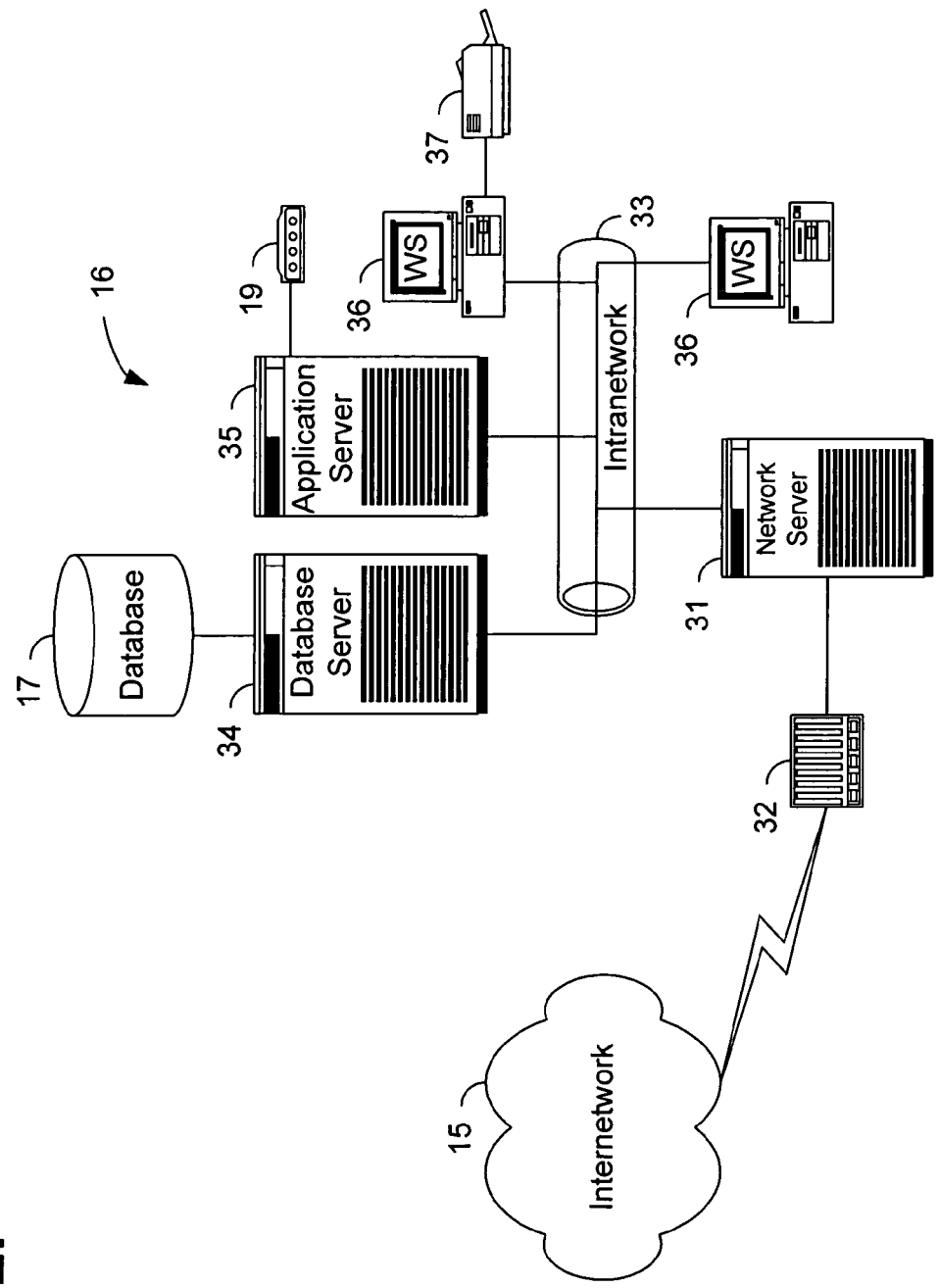
FIG. 2 is a block diagram showing the hardware components of the server system of the system of FIG. 1A.

FIG. 2 is a block diagram showing the hardware components of the server system 16 of the system 10 of FIG. 1A. The server system 16 consists of three individual servers: network server 31, database server 34, and application server 35. These servers are interconnected via an intranetwork 33. In the described embodiment, the functionality of the server system 16 is distributed among these three servers for efficiency and processing speed, although the functionality could also be performed by a single server or cluster of servers. The network server 31 is the primary interface of the server system 16 onto the internetwork 15. The network server 31 periodically receives the collected telemetered signals sent by remote implantable medical devices over the internetwork 15. The network server 31 is interfaced to the internetwork 15 through a router 32. To ensure reliable data exchange, the network server 31 implements a TCP/IP protocol stack, although other forms of network protocol stacks are suitable.

The database server 34 organizes the patient care records in the database 17 and provides storage of and access to information held in those records. A high volume of data in the form of collected device measures sets from individual patients is received. The database server 34 frees the network server 31 from having to categorize and store the individual collected device measures sets in the appropriate patient care record.

The application server 35 operates management applications, assimilates the reference measures into the reference baseline 5 (shown in FIG. 1A), and performs data analysis of the patient care records, as further described below with reference to FIG. 3. The application server 35 communicates feedback to the individual patients either through electronic mail sent back over the internetwork 15 via the network server 31 or as automated voice mail or facsimile messages through the telephone interface device 19.

The server system 16 also includes a plurality of individual workstations 36 (WS) interconnected to the intranetwork 33, some of which can include peripheral devices, such as a printer 37. The workstations 36 are for use by the data management and programming staff, nursing staff, office staff, and other consultants and authorized personnel.

The database 17 consists of a high-capacity storage medium configured to store individual patient care records and related health care information. Preferably, the database 17 is configured as a set of high-speed, high capacity hard drives, such as organized into a Redundant Array of Inexpensive Disks (RAID) volume. However, any form of volatile storage, non-volatile storage, removable storage, fixed storage, random access storage, sequential access storage, permanent storage, erasable storage, and the like would be equally suitable. The organization of the database 17 is further described below with reference to FIGS. 5-7.

The individual servers and workstations are general purpose, programmed digital computing devices consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage. In the described embodiment, the individual servers are Intel Pentium-based server systems, such as available from Dell Computers, Austin, Tex., or Compaq Computers, Houston, Tex. Each system is preferably equipped with 128 MB RAM, 100 GB hard drive capacity, data backup facilities, and related hardware for interconnection to the intranetwork 33 and internetwork 15. In addition, the workstations 36 are also Intel Pentium-based personal computer or workstation systems, also available from Dell Computers, Austin, Tex., or Compaq Computers, Houston, Tex. Each workstation is preferably equipped with 64 MB RAM, 10 GB hard drive capacity, and related hardware for interconnection to the intranetwork 33. Other types of server and workstation systems, including personal computers, minicomputers, mainframe computers, supercomputers, parallel computers, workstations, digital data processors and the like would be equally suitable, as is known in the art.

The telemetered signals are communicated over an internetwork 15, such as the Internet. However, any type of electronic communications link could be used, including an intranetwork link, serial link, data telephone link, satellite link, radio-frequency link, infrared link, fiber optic link, coaxial cable link, television link, and the like, as is known in the art. Also, the network server 31 is interfaced to the internetwork 15 using a T-1 network router 32, such as manufactured by Cisco Systems, Inc., San Jose, Calif. However, any type of interfacing device suitable for interconnecting a server to a network could be used, including a data modem, cable modem, network interface, serial connection, data port, hub, frame relay, digital PBX, and the like, as is known in the art.

Figure 3:
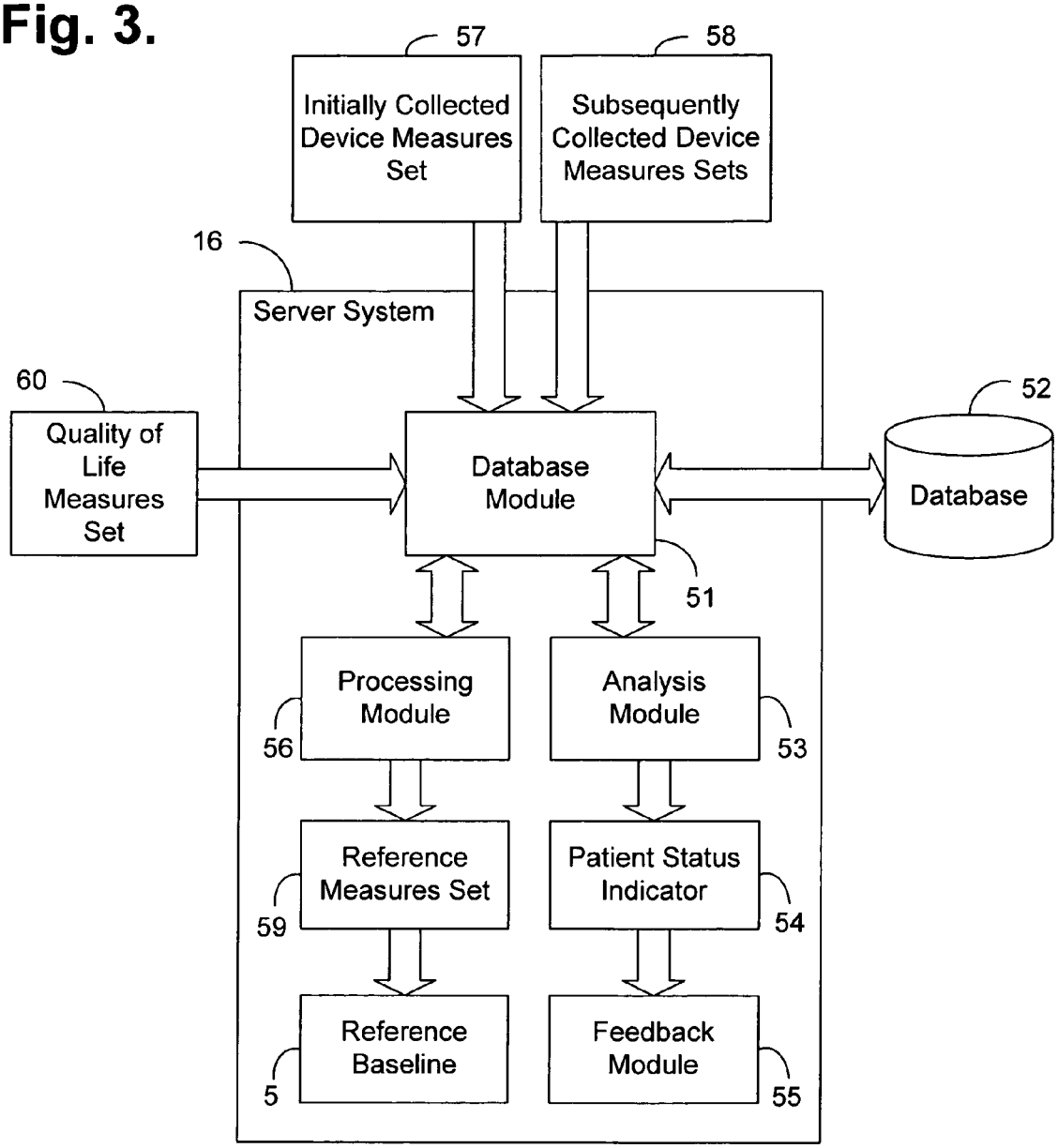
FIG. 3 is a block diagram showing the software modules of the server system of the system of FIG. 1A.

FIG. 3 is a block diagram showing the software modules of the server system 16 of the system 10 of FIG. 1A. Each module is a computer program written as source code in a conventional programming language, such as the C or Java programming languages, and is presented for execution by the CPU as object or byte code, as is known in the art. The various implementations of the source code and object and byte codes can be held on a computer-readable storage medium or embodied on a transmission medium in a carrier wave.

There are three basic software modules, which functionally define the primary operations performed by the server system 16: database module 51, analysis module 53, and processing module 56. In the described embodiment, these modules are executed in a distributed computing environment, although a single server or a cluster of servers could also perform the functionality of these modules. The module functions are further described below beginning with reference to FIGS. 8A-8C.

A reference baseline 5 is established at the outset of providing a patient with remote patient care. The server system 16 periodically receives an initially collected device measures set 57. This set represents patient information which was collected from the implantable medical device 12 (shown in FIG. 1A) during the initial observation period, as further discussed below with reference to FIG. 5. In addition, the server system 16 can also periodically receive quality of life measures sets 60 recorded by the patient 11, as further described below with reference to FIG. 6. Both the initially collected device measures set 57 and quality of life measures set 60 are forwarded to the database module 51 for storage in the patient's patient care record in the database 52. During subsequent, on-going monitoring for remote patient care, the server system 16 periodically receives subsequently collected device measures sets 58, which are also forwarded to the database module 51 for storage.

The database module 51 organizes the individual patent care records stored in the database 52 and provides the facilities for efficiently storing and accessing the collected device measures sets 57, 58 and patient data maintained in those records. Exemplary database schemes for use in storing the initially collected device measures set 57, quality of life measures set 60, and subsequently collected device measures sets 58 in a patient care record are described below, by way of example, with reference to FIGS. 5-7. The database server 34 (shown in FIG. 2) performs the functionality of the database module 51. Any type of database organization could be utilized, including a flat file system, hierarchical database, relational database, or distributed database, such as provided by database vendors, such as Oracle Corporation, Redwood Shores, Calif.

The processing module 56 processes the initially collected device measures set 57 and, if available, the quality of life measures set 60, stored in the patient care records in the database 52 into the reference baseline 5. The reference baseline 5 includes a set of reference measures 59 which can be either directly measured or indirectly derived patient information. The reference baseline 5 can be used to identify patients for whom remote patient care might be inappropriate and to monitor patient wellness in a continuous, on-going basis.

On a periodic basis or as needed, the processing module 56 reassesses the reference baseline 5. Subsequently collected device measures sets 58 are received from the implantable medical device 12 (shown in FIG. 1A) subsequent to the initial observation period. The processing module 56 reassimilates these additional collected device measures sets into a new reference baseline. The operations performed by the processing module 56 are further described below with reference to FIG. 4. The application server 35 (shown in FIG. 2) performs the functionality of the processing module 56.

The analysis module 53 analyzes the subsequently collected device measures sets 58 stored in the patient care records in the database 52. The analysis module 53 monitors patient wellness and makes an automated determination in the form of a patient status indicator 54. Subsequently collected device measures sets 58 are periodically received from implantable medical devices and maintained by the database module 51 in the database 52. Through the use of this collected information, the analysis module 53 can continuously follow the medical well being of a patient and can recognize any trends in the collected information that might warrant medical intervention. The analysis module 53 compares individual measures and derived measures obtained from both the care records for the individual patient and the care records for a disease specific group of patients or the patient population in general. The analytic operations performed by the analysis module 53 are further described below with reference to FIG. 4. The application server 35 (shown in FIG. 2) performs the functionality of the analysis module 53.

The feedback module 55 provides automated feedback to the individual patient based, in part, on the patient status indicator 54. As described above, the feedback could be by electronic mail or by automated voice mail or facsimile. Preferably, the feedback is provided in a tiered manner. In the described embodiment, four levels of automated feedback are provided. At a first level, an interpretation of the patient status indicator 54 is provided. At a second level, a notification of potential medical concern based on the patient status indicator 54 is provided. This feedback level could also be coupled with human contact by specially trained technicians or medical personnel. At a third level, the notification of potential medical concern is forwarded to medical practitioners located in the patient's geographic area. Finally, at a fourth level, a set of reprogramming instructions based on the patient status indicator 54 could be transmitted directly to the implantable medical device to modify the programming instructions contained therein. As is customary in the medical arts, the basic tiered feedback scheme would be modified in the event of bona fide medical emergency. The application server 35 (shown in FIG. 2) performs the functionality of the feedback module 55.

Figure 4:
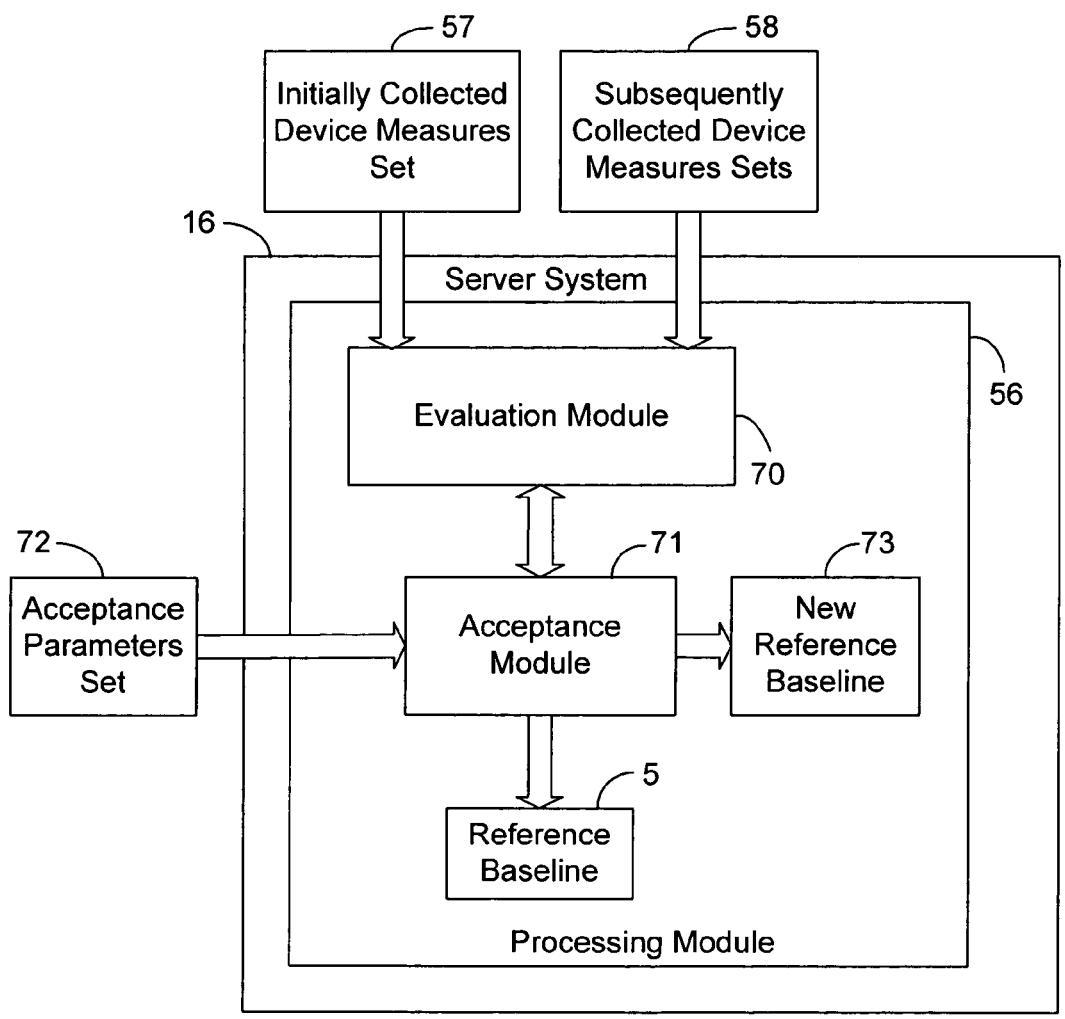
FIG. 4 is a block diagram showing the processing module of the server system of FIG. 1A.

FIG. 4 is a block diagram showing the processing module 56 of the server system 16 of FIG. 1A. The processing module 53 contains two functional submodules: evaluation module 70 and acceptance module 71. The purpose of the evaluation module 70 is to process the initially collected device measures set 57 by determining any derived measures and calculating appropriate statistical values, including means and standard deviations, for the reference measures set 59 in the reference baseline 5. The purpose of the acceptance module 71 is to analyze the reference measures set 59 against the acceptance parameters set 72. A patient care record storing a reference measures set 59 substantially out of conformity with the acceptance parameters set 72 could be indicative of a patient for whom remote patient care is inappropriate. Consequently, the acceptance module 71 identifies each patient care record storing at least one reference measure, which is substantially non-conforming to a corresponding parameter in the acceptance parameters set 72.

For instance, an acceptance parameter for heart rate might be specified as a mean heart rate within a range of 40-90 beats per minute (bpm) over a 24-hour period. However, a patient care record storing a reference measure falling either substantially above or below this acceptance parameter, for example, in excess of 90 bpm, would be considered substantially non-conforming. The acceptance parameters set 72 are further described below with reference to FIG. 5.

The evaluation module 70 also determines new reference baselines 73 when necessary. For instance, the new reference baseline 73 might be reassessed on an annual or quarterly basis, as the needs of the patient 11 dictate. Similarly, the new reference baseline 73 might be reassessed for a patient whose patient care record stores a subsequently collected device measures set 58 substantially out of conformity with the reference measures set 59 in the original reference baseline 5. The new reference baseline 73 would be assessed by the processing module 56 using subsequently collected device measures sets 58 during a subsequent observation period.

Figure 5:
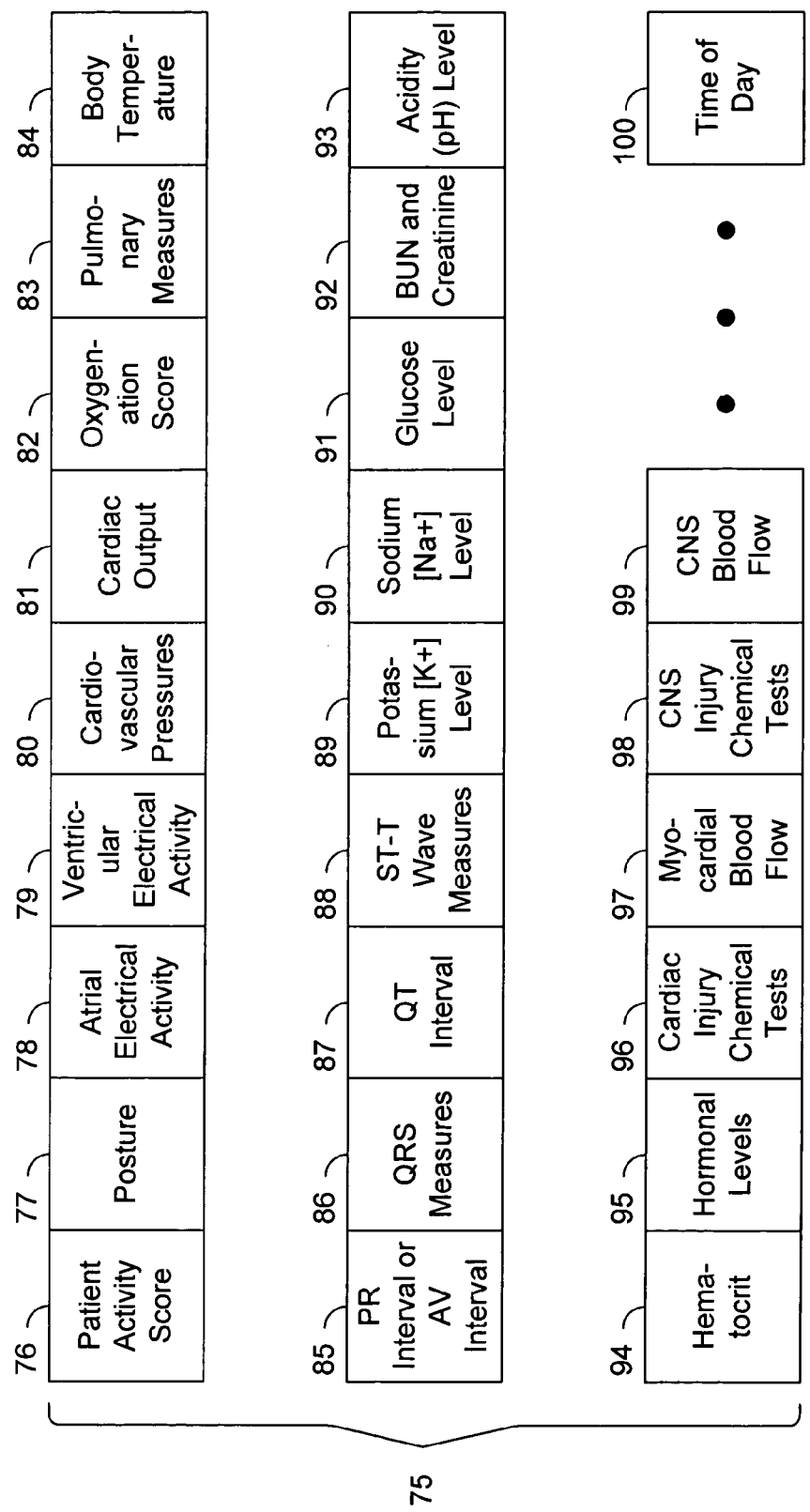
FIG. 5 is a database schema showing, by way of example, the organization of a reference baseline record for cardiac patient care stored as part of a patient care record in the database of the system of FIG. 1A.

FIG. 5 is a database schema showing, by way of example, the organization of a reference baseline record 75 for cardiac patient care stored as part of a patient care record in the database 17 of the system 10 of FIG. 1A. The reference baseline record 75 corresponds to the reference baseline 5, although only the information pertaining to the set of reference measures in the reference baseline 5 are shown. Each patient care record would also contain normal identifying and treatment profile information, as well as medical history and other pertinent data (not shown). For instance, during the initial observation period, the patient 11 maintains a diary of activities, including the onset of bedtime and waking time, plus the time and dosing of any medications, including non-prescription drugs. The observation period can be expanded to include additional information about the normal range of patient activities as necessary, including a range of potential anticipated activities as well as expected travel times and periods away from home. In addition, information from any set of medical records could be included in the patient care record. The diary, medication, activity, and medical record information and medical test information (e.g., electrocardiogram, echocardiogram, and/or coronary angiogram) is incorporated into the patient care record and is updated with continuing patient information, such as changes in medication, as is customary in the art.

The reference measures set 59 stored in the reference baseline record 75 are processed from the initial collected device measures set 57 (shown in FIG. 3), as further described below with reference to FIG. 9. The implantable medical device 12 (shown in FIG. 1A) records the initial collected device measures set 57 during the initial observation period. For example, for a cardiac patient, the reference baseline record 75 stores the following information as part of the reference measures set 59: patient activity score 76, posture 77 (e.g., from barometric pressure), atrial electrical activity 78 (e.g., atrial rate), ventricular electrical activity 79 (e.g., ventricular rate), cardiovascular pressures 80, cardiac output 81, oxygenation score 82 (e.g., mixed 30 venous oxygenation), pulmonary measures 83 (e.g., transthoracic impedance, measures of lung wetness, and/or minute ventilation), body temperature 84, PR interval 85 (or AV interval), QRS measures 86 (e.g., width, amplitude, frequency content, and/or morphology), QT interval 87, ST-T wave measures 88 (e.g., T wave alternans or ST segment depression or elevation), potassium [K+] level 89, sodium [Na+] level 90, glucose level 91, blood urea nitrogen and creatinine 92, acidity (pH) level 93, hematocrit 94, hormonal levels 95 (e.g., insulin, epinephrine), cardiac injury chemical tests 96 (e.g., troponin, myocardial band creatinine kinase), myocardial blood flow 97, central nervous system injury chemical tests 98 (e.g., cerebral band creatinine kinase), central nervous system (CNS) blood flow 99, and time of day 100. Other types of reference measures are possible. In addition, a well-documented set of derived measures can be determined based on the reference measures, as is known in the art.

In the described embodiment, the initial and any subsequent observation periods last for about one 7-day period during which time the patient 11 might be asked to perform, if possible, repeated physical stressors representative of both relatively normal activity and/or activities designed to test the response of the body to modest activity and physiologic perturbations for use as the baseline "reference" measures that might be recorded daily for a period of one week prior to initiating fee-for-service monitoring. Reference measures taken and derived from the observation period are recorded, processed, and stored by the system 10. The reference measures include both measured and derived measures, including patient activity score 76, posture 77, atrial electrical activity 78, ventricular electrical activity 79, cardiovascular pressures 80, cardiac output 81, oxygenation score 82, pulmonary measures 83, body temperature 84, PR interval 85 (or AV interval), QRS measures 86, QT interval 87, ST-T wave measures 88, potassium [K+] level 89, sodium [Na+] level 90, glucose level 91, blood urea nitrogen and creatinine 92, acidity (pH) level 93, hematocrit 94, hormonal levels 95, cardiac injury chemical tests 96, myocardial blood flow 97, central nervous system injury chemical tests 98, central nervous system (CNS) blood flow 99, and time of day 100. Other combination and derivative measures can also be determined, as known in the art.

An illustrative prescribed set of timed physical stressors for a non-ambulatory patient 11 is as follows:

(1) Running in place 6: if possible, the patient 11 must run in place for about five minutes;
(2) Walking (not shown): if possible, the patient 11 must walk for about six minutes and the total distance walked is measured;
(3) Ascending stairs (not shown): if possible, the patient 11 must ascend two flights of stairs;
(4) Recumbency 7: if possible, the patient 11 must recline following about two minutes of motionless immobile upright posture. Upon recumbency, the patient 11 must remain as immobile as possible for about ten minutes;
(5) Standing 8: if possible, the patient 11 must briskly assume an upright standing posture after the ten-minute recumbency 7 and must remain standing without activity for about five minutes;
(6) Coughing (not shown): if possible, the patient 11 must cough forcefully about three times when in an upright position to record the cardiovascular pressures 80;
(7) Hyperventilation (not shown): if possible, the patient 11 must hyperventilate over thirty seconds with full deep and rapid breaths to record ventilatory status;
(8) Sitting motionless 9: when a physician is complicit, the patient 11 must, if possible, use an approximately 2.0 liter per minute nasal cannula while transmitting data for about twenty minutes while sitting to evaluate cardiopulmonary response;
(9) Program AAI and VVI temporary pacing interventions for five minutes, at low and high rates, if applicable (e.g., 40 bpm and 120 bpm) to evaluate cardiopulmonary response; and
(10) Test dual site or biventricular pacing modes, if applicable, for approximately 20 minutes to evaluate cardiopulmonary response.

These physical and pacing stimulus stressors must be annotated with date and time of day 100 and correlated with symptoms and the quality of life measures 110. Heart rate, temperature, and time of day are directly measured while the patient activity score and cardiac output score are derived. These physical stressors are merely illustrative in nature and the set of physical and pacing stimulus stressors actually performed by any given patient would necessarily depend upon their age and physical condition as well as device implanted. Also, during the observation period, the temperature is monitored with QT interval shortening and, if the patient is in atrial fibrillation, the patient 11 must undergo an incremental ventricular pacing protocol to assess his or her response to rate stabilization. Finally, a T-wave alternans measurement (not shown) can be integrated into the reference baseline 5 during rest and sinus rhythm activities.

In a further embodiment of the present invention, the reference measures set 59 in the reference baseline 5 are reassessed on an annual or, if necessary, quarterly, basis. In addition, if the reference measures set 59 was recorded during a period when the patient 11 was unstable or recovering from a recent illness, the reference baseline 5 is reassessed when the patient 11 is again stable, as further described below with reference to FIG. 11.

As further described below with reference to FIG. 9, the reference measures are analyzed against the acceptance parameters set 72. The acceptance parameters are those indicator values consistent with the presence of some form of chronic yet stable disease, which does not require immediate emergency care.

In the described embodiment, the acceptance parameters set 72 for the reference measures 59 in the reference baseline record 75 are, by way of example, as follows: cardiac output 81 falling below 2.5 liters/minute/m2; heart rate below 40 bpm or above 120 bpm; body temperature 84 over 101° F. and below 97° F.; patient activity 76 score of 1.0 or below; oxygenation score 82 of less than 60% mixed venous saturation at rest; pulmonary artery diastolic pressure greater than 20 mm Hg at rest; and minute ventilation less than 10.0 liters/minute at rest.

FIG. 6 is a database schema showing, by way of example, the organization of a reference baseline quality of life record 110 for cardiac patient care stored as part of a patient care record in the database 17 of the system 10 of FIG. 1A. A quality of life score is a semi-quantitative self-assessment of an individual patient's physical and emotional well being. Non-commercial, non-proprietary standardized automated quality of life scoring systems are readily available, such as provided by the Duke Activities Status Indicator. These scoring systems can be provided for use by the patient 11 on the personal computer 18 (shown in FIG. 1A) and the patient 11 can then record his or her quality of life scores for periodic download to the server system 16.

For example, for a cardiac patient, the reference baseline quality of life record 110 stores the following information as part of the reference measures set 59: health wellness 111, shortness of breath 112, energy level 113, exercise tolerance 114, chest discomfort 115, time of day 116, and other quality of life measures as would be known to one skilled in the art. Using the quality of life scores 111-116 in the reference baseline quality of life record 110, the patient 11 can be notified automatically when variable physiological changes matches his or her symptomatology.

A quality of life indicator is a vehicle through which a patient can remotely communicate to the patient care system how he or she is subjectively feeling. When tied to machine-recorded physiological measures, a quality of life indicator can provide valuable additional information to medical practitioners and the automated collection and analysis patient care system 10 not otherwise discernible without having the patient physically present. For instance, a scoring system using a scale of 1.0 to 10.0 could be used with 10.0 indicating normal wellness and 1.0 indicating severe health problems. Upon the completion of the initial observation period, a patient might indicate a health wellness score 111 of 5.0 and a cardiac output score of 5.0. After one month of remote patient care, the patient might then indicate a health wellness score 111 of 4.0 and a cardiac output score of 4.0 and a week later indicate a health wellness score 111 of 3.5 and a cardiac output score of 3.5. Based on a comparison of the health wellness scores 111 and the cardiac output scores, the system 10 would identify a trend indicating the necessity of potential medical intervention while a comparison of the cardiac output scores alone might not lead to the same prognosis.

FIG. 7 is a database schema showing, by way of example, the organization of a monitoring record 120 for cardiac patient care stored as part of a patient care record in the database 17 of the system 10 of FIG. 1A. Each patient care record stores a multitude of subsequently collected device measures sets 58 (shown in FIG. 3) for each individual patient 11. Each set represents a recorded snapshot of telemetered signals data which were recorded, for instance, on a per heartbeat or binned average basis by the implantable medical device 12. For example, for a cardiac patient, the following information would be recorded as a subsequently collected device measures set 58: atrial electrical activity 121, ventricular electrical activity 122, minute ventilation 123, patient activity score 124, cardiac output score 125, mixed venous oxygen score 126, pulmonary artery diastolic pressure measure 127, time of day 128, interventions made by the implantable medical device 129, and the relative success of any interventions made 130. In addition, the implantable medical device 12 would also communicate device specific information, including battery status and program settings 131. Other types of collected or combined measures are possible as previously described. In addition, a well-documented set of derived measures can be determined based on the collected measures, as is known in the art.

Figure 8A:
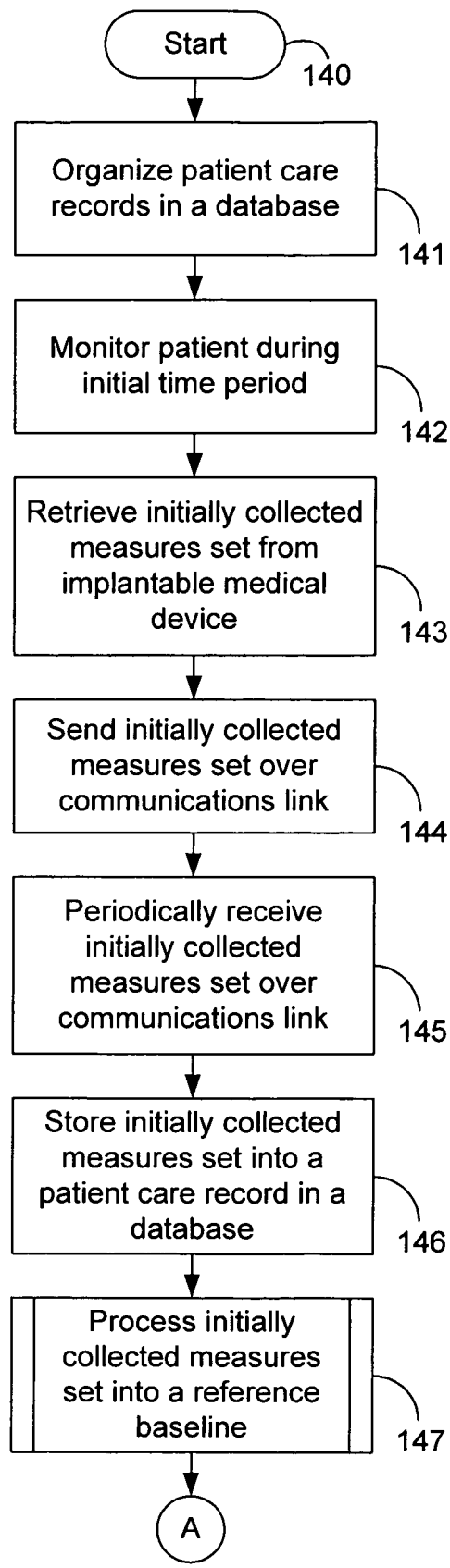
FIGS. 8A-8C are flow diagrams showing a method for determining a reference baseline for use in monitoring a patient status in an automated collection and analysis patient care system in accordance with the present invention.
Figure 8B:
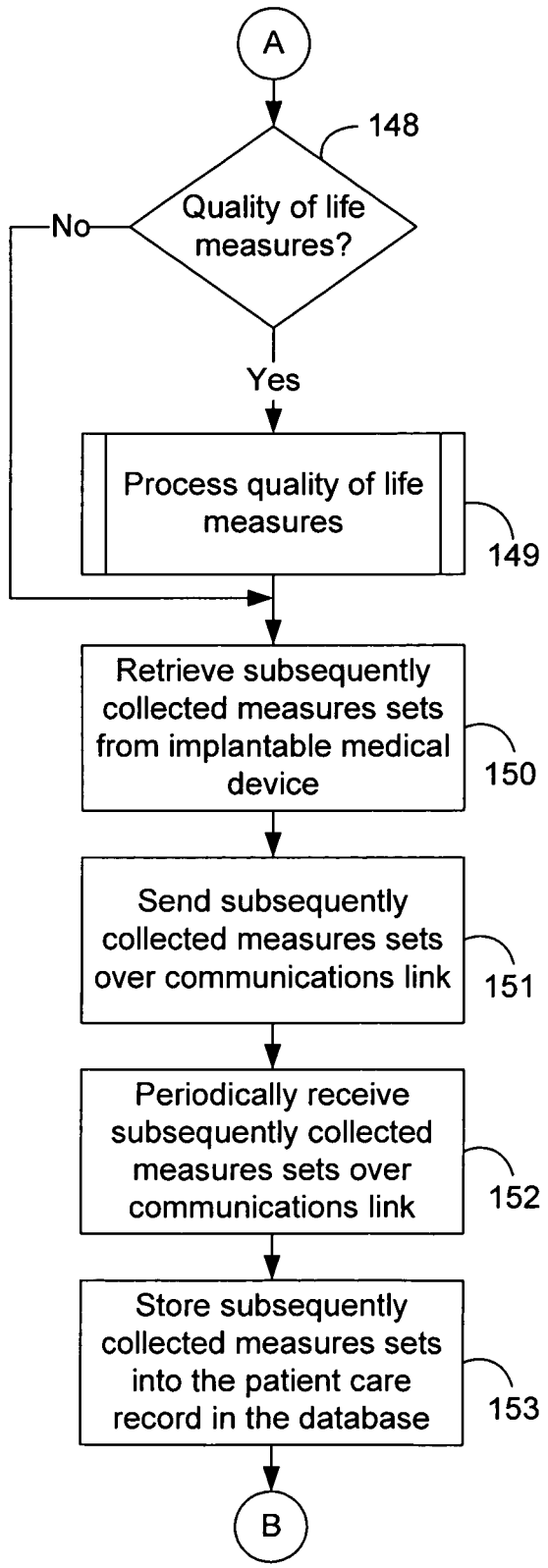
Figure 8C:
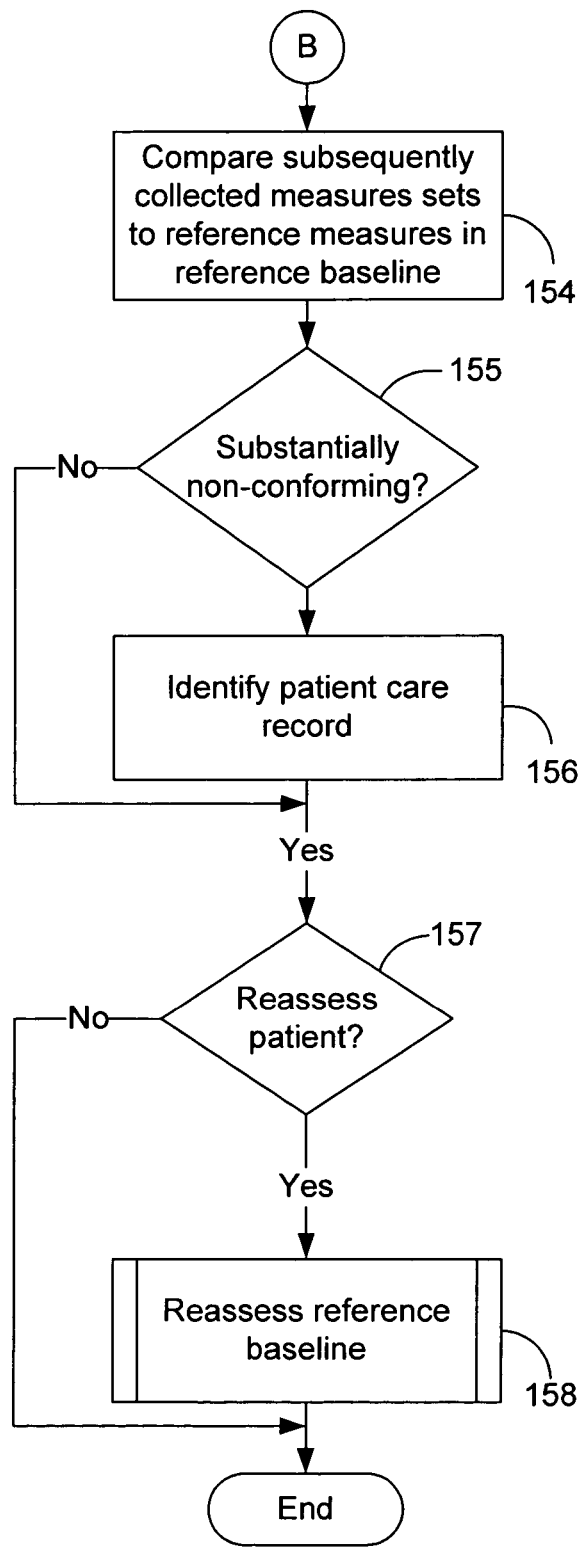

FIGS. 8A-8C are flow diagrams showing a method 140 for determining a reference baseline 5 for use in monitoring a patient status in an automated collection and analysis patient care system 10 in accordance with the present invention. The method 140 operates in two phases: collection and processing of an initial reference baseline 5 (blocks 141-149) and monitoring using the reference baseline 5 (blocks 150-158). The method 140 is implemented as a conventional computer program for execution by the server system 16 (shown in FIG. 1A). As a preparatory step, the patient care records are organized in the database 17 with a unique patient care record assigned to each individual patient (block 141).

The collection and processing of the initial reference baseline 5 begins with the patient 11 being monitored by the implantable medical device 12 (shown in FIG. 1A). The implantable medical device 12 records the initially collected device measures set 57 during the initial observation period (block 142), as described above with reference to FIG. 5. Alternatively, the patient 11 could be engaged in performing the prescribed set of timed physical stressors during the initial observation period, as described above with reference to FIG. 1B. As well, the implantable medical device 12 could be reprogrammed by the programmer 14 during the initial observation period, also as described above with reference to FIG. 1B. The initially collected device measures set 57 is retrieved from the implantable medical device 12 (block 143) using a programmer, interrogator, telemetered signals transceiver, and the like. The retrieved initially collected device measures sets are sent over the internetwork 15 or similar communications link (block 144) and periodically received by the server system 16 (block 145). The initially collected device measures set 57 is stored into a patient care record in the database 17 for the individual patient 11 (block 146). The initially collected device measures set 57 is processed into the reference baseline 5 (block 147) which stores a reference measures set 59, as further described below with reference to FIG. 9.

If quality of life measures are included as part of the reference baseline 5 (block 148), the set of quality of life measures are processed (block 149), as further described below with reference to FIG. 10. Otherwise, the processing of quality of life measures is skipped (block 148).

Monitoring using the reference baseline 5 begins with the retrieval of the subsequently collected device measures sets 58 from the implantable medical device 12 (block 150) using a programmer, interrogator, telemetered signals transceiver, and the like. The subsequently collected device measures sets 58 are sent, on a substantially regular basis, over the internetwork 15 or similar communications link (block 151) and periodically received by the server system 16 (block 152). The subsequently collected device measures sets 58 are stored into the patient care record in the database 17 for that individual patient (block 153).

The subsequently collected device measures sets 58 are compared to the reference measures in the reference baseline 5 (block 154). If the subsequently collected device measures sets 58 are substantially non-conforming (block 155), the patient care record is identified (block 156). Otherwise, monitoring continues as before.

In the described embodiment, substantial non-conformity refers to a significant departure from a set of parameters defining ranges of relative normal activity and normal exercise responses for that patient. Relative normal activity is defined as follows. Note the "test exercise period" refers to running in place, walking, and ascending stairs physical stressors described above:

(1) Heart rate stays within a range of 40-90 bpm without upward or downward change in mean heart rate (1.0 standard deviation (SD) over a 24 hour period;

(2) Wake patient activity score during awake hours stays within a range of (1.0 SD without change in the mean activity score over a 24 hour period with no score equal to the minimum activity score noted during sleep;

(3) Sleep period activity score stays within a range of (1.0 SD of typical sleep scores for that patient for the six to ten hour period of sleep with no score less than the minimum score observed during normal awake behavior during the initial observation period or during normal sleep;

(4) Minute ventilation 123 during normal awake hours stays within a range of (1.0 SD without change in the mean score over a 24 hour period with no score equal to the minimum or maximum minute ventilation 123 noted during the test exercise period or the minimum or maximum minute ventilation 123 noted during the initial observation period;

(5) Cardiac output score 125 during normal awake hours stays within a range of (1.0 SD without change in the mean cardiac output score over a 24 hour period with no score equal to the minimum cardiac output score noted during the test exercise period or the minimum cardiac output score noted during the initial observation period;

(6) Mixed venous oxygenation score 126 during normal awake hours stays within a range of (1.0 SD without change in the mean mixed venous oxygenation score over a 24 hour period with no score equal to the minimum mixed venous oxygenation score noted during the test exercise period or the minimum mixed venous oxygenation score noted during the initial observation period;

(7) Pulmonary artery diastolic pressure measure 127 during normal awake hours stays within a range of (1.0 SD without change in the mean pulmonary artery diastolic pressure measure 127 over a 24 hour period with no score equal to the minimum or maximum pulmonary artery diastolic pressure measure 127 noted during the test exercise period or during the initial observation period;

(8) Potassium levels [K+] score during normal awake hours stays within a range of (1.0 SD without change in the mean K+ levels over a 24 hour period with no score less than 3.5 meq/liter or greater than 5.0 meq/liter noted during the test exercise period or during the initial observation period;

(9) Sodium levels [Na+] score during normal awake hours stays within a range of (1.0 SD without change in the mean Na+ levels over a 24 hour period with no score less than 135 meq/liter or greater than 145 meq/liter during the test exercise period or during the initial observation period;

(10) Acidity (pH) score during normal awake hours stays within a range of (1.0 SD without change in the mean pH score over a 24 hour period with no score equal to the minimum or maximum pH score noted during the test exercise period or the minimum or maximum pH scores noted during the initial observation period;

(11) Glucose levels during normal awake hours stays within a range of ( 1.0 SD without change in the mean glucose levels over a 24 hour period with no score less than 60 mg/dl or greater than 200 /dl during the test exercise period or during the initial observation period;

(12) Blood urea nitrogen (BUN) or creatinine (Cr) levels during normal awake hours stays within a range of (1.0 SD without change in the mean BUN or Cr levels score over a 24 hour period with no score equal to the maximum BUN or creatinine levels noted during the test exercise period or the maximum BUN or Cr levels noted during the initial observation period;

(13) Hematocrit levels during normal awake hours stays within a range of (1.0 SD without change in the mean hematocrit levels score over a 24 hour period with no score less than a hematocrit of 30 during the test exercise period or during the initial observation period;

(14) Troponin, creatinine kinase myocardial band, or other cardiac marker of myocardial infarction or ischemia, level during normal awake hours stays within a range of (1.0 SD without change in the mean troponin level score over a 24 hour period with no score equal to the maximum troponin level score noted during the test exercise period or the maximum troponin level scores noted during the initial observation period;

(15) Central nervous system (CNS) creatinine kinase (CK) or equivalent markers of CNS ischemia or infarction levels during normal awake hours stays within a range of (1.0 SD without change in the mean CNS CK levels over a 24 hour period with no score equal to the maximum CNS CK levels score noted during the test exercise period or the maximum CNS CK levels scores noted during the initial observation period;

(16) Barometric pressure during normal awake hours stays within a range of (1.0 SD without change in the mean barometric pressure score over a 24 hour period with no score equal to the minimum or maximum barometric pressure noted during the test exercise period or the minimum or maximum barometric pressure noted during the initial observation period;

(17) PR interval (or intrinsic AV interval) of sinus rhythm during normal awake hours stays within a range of (1.0 SD without change in the mean PR interval over a 24 hour period with no score equal to the minimum or maximum PR interval noted during the test exercise period or the minimum or maximum PR interval noted during the initial observation period;

(18) QT interval during normal awake hours stays within a range of ( 1.0 SD without change in the mean QT interval over a 24 hour period with no score equal to the minimum or maximum QT interval noted during the test exercise period or the minimum or maximum QT interval noted during the initial observation period;

(19) QRS duration during normal awake hours stays within a range of ( 1.0 SD without change in the mean QRS duration over a 24 hour period with no score equal to the maximum QRS duration noted during the test exercise period or the maximum QRS duration noted during the initial observation period;

(20) ST segment depression or elevation during normal awake hours stays within a range of (1.0 SD without change in the mean ST segment depression or elevation over a 24 hour period with no score equal to the maximum ST segment depression or elevation noted during the test exercise period or the maximum ST segment depression or elevation noted during the initial observation period; and

(21) Temperature during normal awake hours stays within a range of ( 1.0 SD without change in the mean temperature over a 24 hour period with no score equal to the minimum or maximum temperature score noted during the test exercise period or the minimum or maximum temperature noted during the initial observation period.

For an exemplary, non-ambulatory patient with no major impairments of the major limbs, reference exercise can be defined as follows:

(1) Heart rate increases by 10 bpm for each one point increase in activity score. Note that to be considered "normal exercise," heart rate generally should not increase when the activity score does not increase at least 1.0 SD above that noted during the twenty-four hour reference period or greater than that observed during any reference exercise periods. Heart rate should decrease to the baseline value over fifteen minutes once activity stops or returns to the baseline activity level;

(2) Patient activity score 124 rises at least 1.0 SD over that observed in the mean activity score over a 24 hour period or greater than that observed during any reference exercise periods;

(3) Cardiac output score 125 rises at least 1.0 SD over that observed in the mean cardiac output score over a 24 hour period or within 0.5 SD of the two minute test exercise period. Cardiac output score should increase 0.5 liters per minute with each 10 bpm increase in heart rate period or greater than that observed during any reference exercise periods;

(4) In conjunction with an increase in activity score and heart rate, mixed venous oxygenation score 126 falls at least 1.0 SD below observed in the mean oxygenation score over a 24 hour period or be less than any oxygenation score observed during the reference exercise periods. Oxygenation score should decrease 5.0 mm Hg with each 10 bpm increase in heart rate or 1.0 SD increase in cardiac output score during exercise;

(5) In conjunction with an increase in activity score and heart rate, pulmonary artery diastolic pressure measure 127 rises at least 1.0 SD over that observed in the mean cardiovascular pressure score over a 24 hour period or is greater than that observed during the reference exercise periods;

(6) In conjunction with an increase in activity score and heart rate, minute ventilation 123 rises at least 1.0 SD over that observed over a 24 hour reference period or greater than that observed during any reference exercise period. Minute ventilation should rise 1.0 liter per minute with each 10 bpm increase in heart rate; and (7) In conjunction with an increase in activity score and heart rate, temperature should rise at least 1.0 SD over that observed in the mean temperature over a 24 hour period or greater than that observed during the reference exercise periods. Temperature should rise 0.1° F. with each 10 bpm increase in heart rate.

Finally, if the time for a periodic reassessment has arrived or the subsequently collected device measures sets 58 are substantially non-conforming (block 157), the reference baseline 5 is reassessed (block 158) and a new reference baseline 73 determined, as further described below with reference to FIG. 11. Otherwise, the routine returns.

In the described embodiment, the reference baseline 5 is preferably reassessed on an annual or, if necessary, quarterly basis. In addition, the reference baseline 5 might be reassessed if physiological findings dictate that new interventions might be indicated or if the patient 11 indicates a change in medications and general health status. Other bases for reassessing the reference baseline 5 are feasible.

Figure 9:
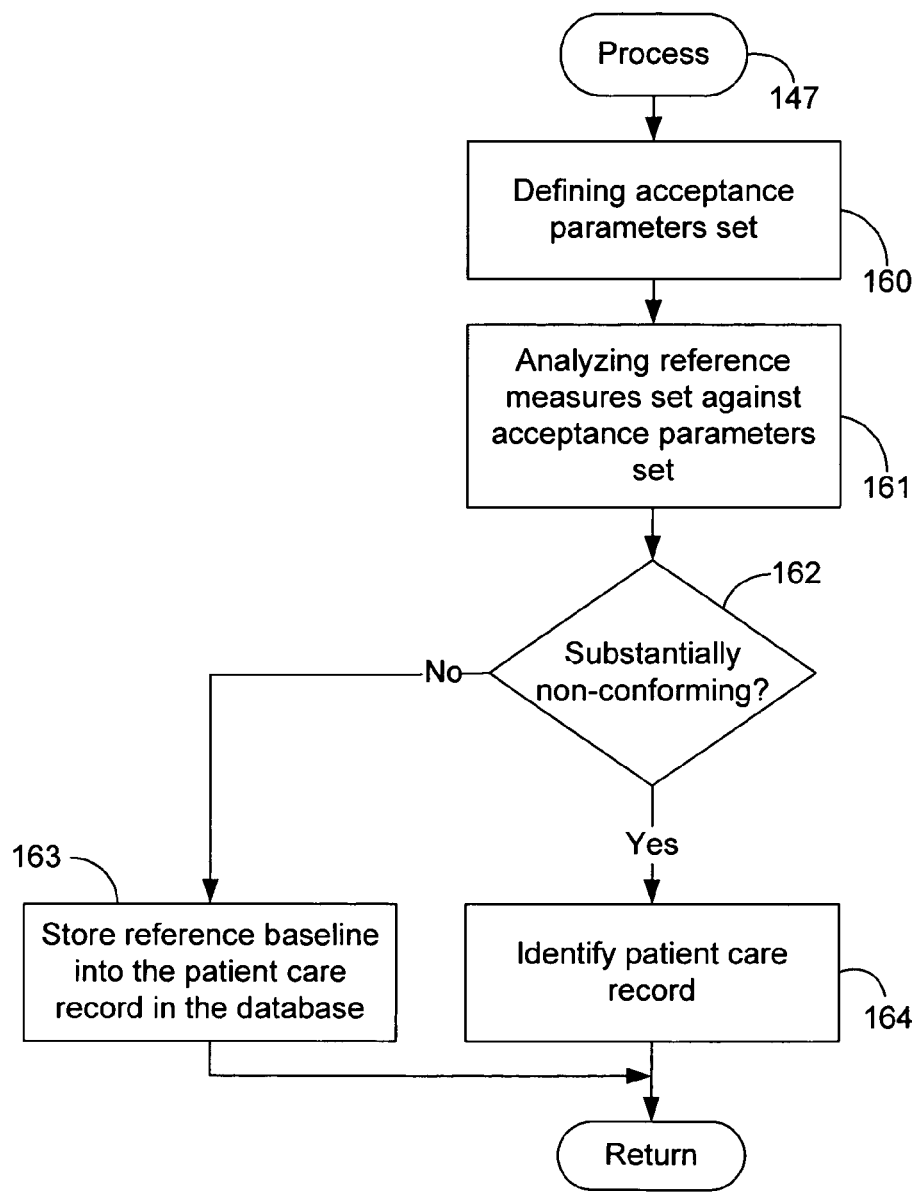
FIG. 9 is a flow diagram showing the routine for processing a reference baseline for use in the method of FIGS. 8A-8C.

FIG. 9 is a flow diagram showing the routine 147 for processing a reference baseline 5 for use in the method 140 of FIGS. 8A-8C. The purpose of this routine is to analyze the initially collected device measures set 57 and create a reference baseline 5, if possible. First, the acceptance parameters set 72 (shown in FIG. 3) is defined (block 160) and the reference measures set 59 in the reference baseline 5, including any quality of life measures, are analyzed against the acceptance parameters set (block 161), as described above with reference to FIG. 5. If the reference measures in the reference baseline 5 are substantially non-conforming to the acceptance parameters set (block 162), the patient care record is identified (block 164). Otherwise, if conforming (block 162), the baseline reference 72 is stored into the patient care record in the database 17 (block 163). The routine then returns.

Figure 10:
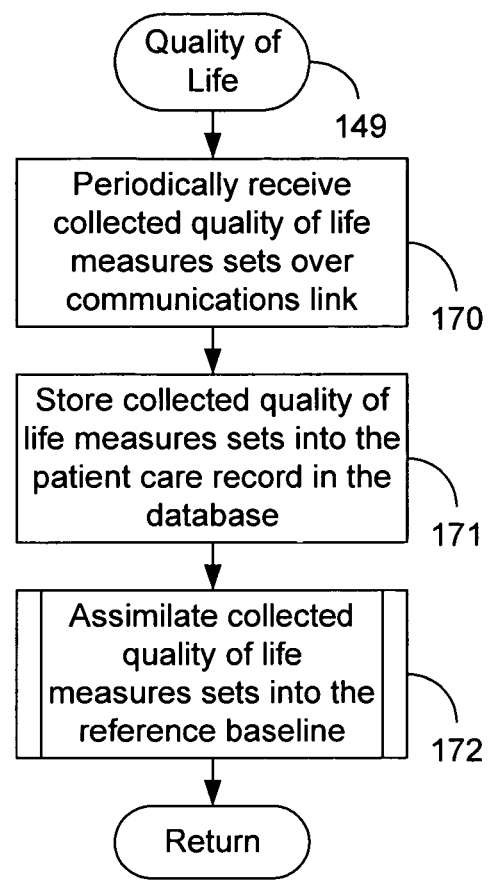
FIG. 10 is a flow diagram showing the routine for processing quality of life measures for use in the method of FIGS. 8A-8C.

FIG. 10 is a flow diagram showing the routine 149 for processing quality of life measures for use in the method 140 of FIGS. 8A-8C. The purpose of this routine is to process and store a collected quality of life measures set 60 into the reference baseline 5. Collected quality of life measures sets 60 are periodically received by the server system 16 over the internetwork 15 or similar communications link (block 170). The quality of life measures were previously recorded by the patient 11 using, for example, the personal computer 18 (shown in FIG. 1A) and downloaded onto the internetwork 15 or similar communications link. The collected quality of life measures set 60 is stored into a patient care record in the database 17 for the individual patient 11 (block 171). The collected quality of life measures set 60 is then assimilated into the reference baseline 5 (block 172), as further described above with reference to FIG. 9. The routine then returns.

Figure 11:
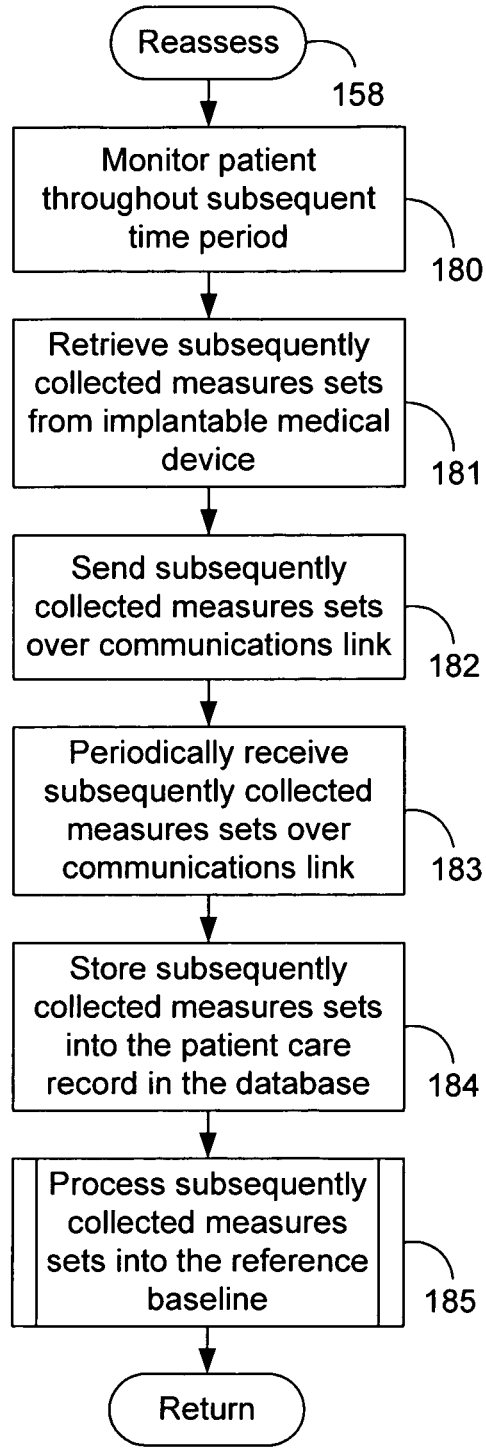
FIG. 11 is a flow diagram showing the routine for reassessing a new reference baseline for use in the method of FIGS. 8A-8C.

FIG. 11 is a flow diagram showing the routine 158 for reassessing a new reference baseline 73 for use in the method 140 of FIGS. 8A-8C. The purpose of this routine is to reassess a new reference baseline 5 periodically or when necessary. Similar to the collection and assimilation of the initial reference baseline 5, the routine begins with the patient 11 being monitored by the implantable medical device 12 (shown in FIG. 1A). The implantable medical device 12 records subsequently collected device measures sets 58 throughout a subsequent observation period (block 180), as described above with reference to FIG. 5. Alternatively, the patient 11 could be engaged in performing the prescribed set of timed physical stressors, as described above with reference to FIG. 1B. As well, the implantable medical device 12 could be reprogrammed by the programmer 14 during the subsequent observation period, also as described above with reference to FIG. 1B. The subsequently collected device measures sets 58 are retrieved from the implantable medical device 12 (block 181) using a programmer, interrogator, telemetered signals transceiver, and the like. The retrieved subsequently collected device measures sets are sent over the internetwork 15 or similar communications link (block 182) and periodically received by the server system 16 (block 183). The subsequently collected device measures sets 58 are stored into the patient care record in the database 17 for the individual patient 11 (block 184). Finally, the subsequently collected device measures sets 58 are assimilated into the new reference baseline 73 (block 185), as further described above with reference to FIG. 9. The routine then returns.

Figure 12A:
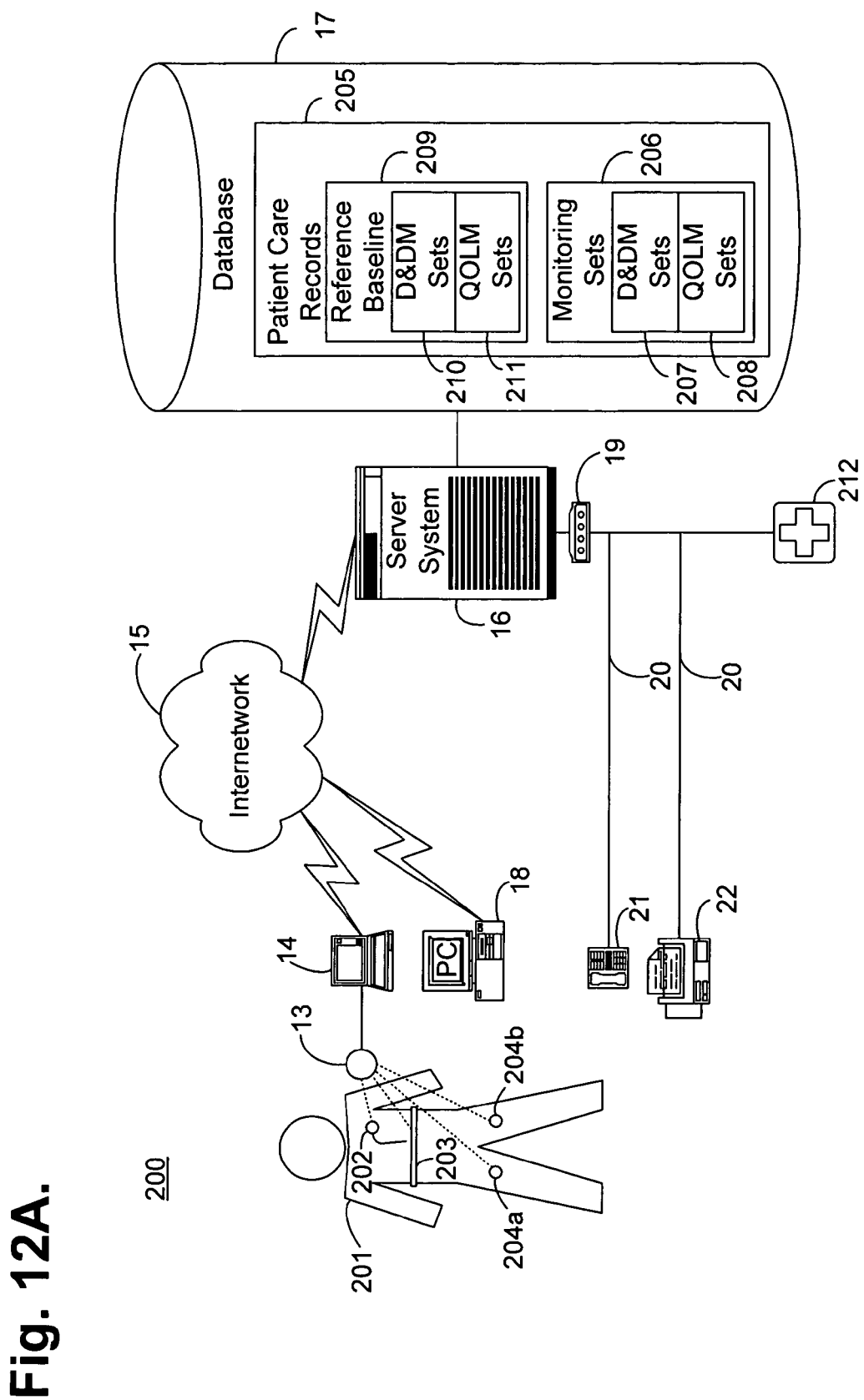
FIGS. 12A and 12B are block diagrams showing system for determining a reference baseline of individual patient status for use in an automated collection and analysis patient care system in accordance with a further embodiment of the present invention.
Figure 12B:
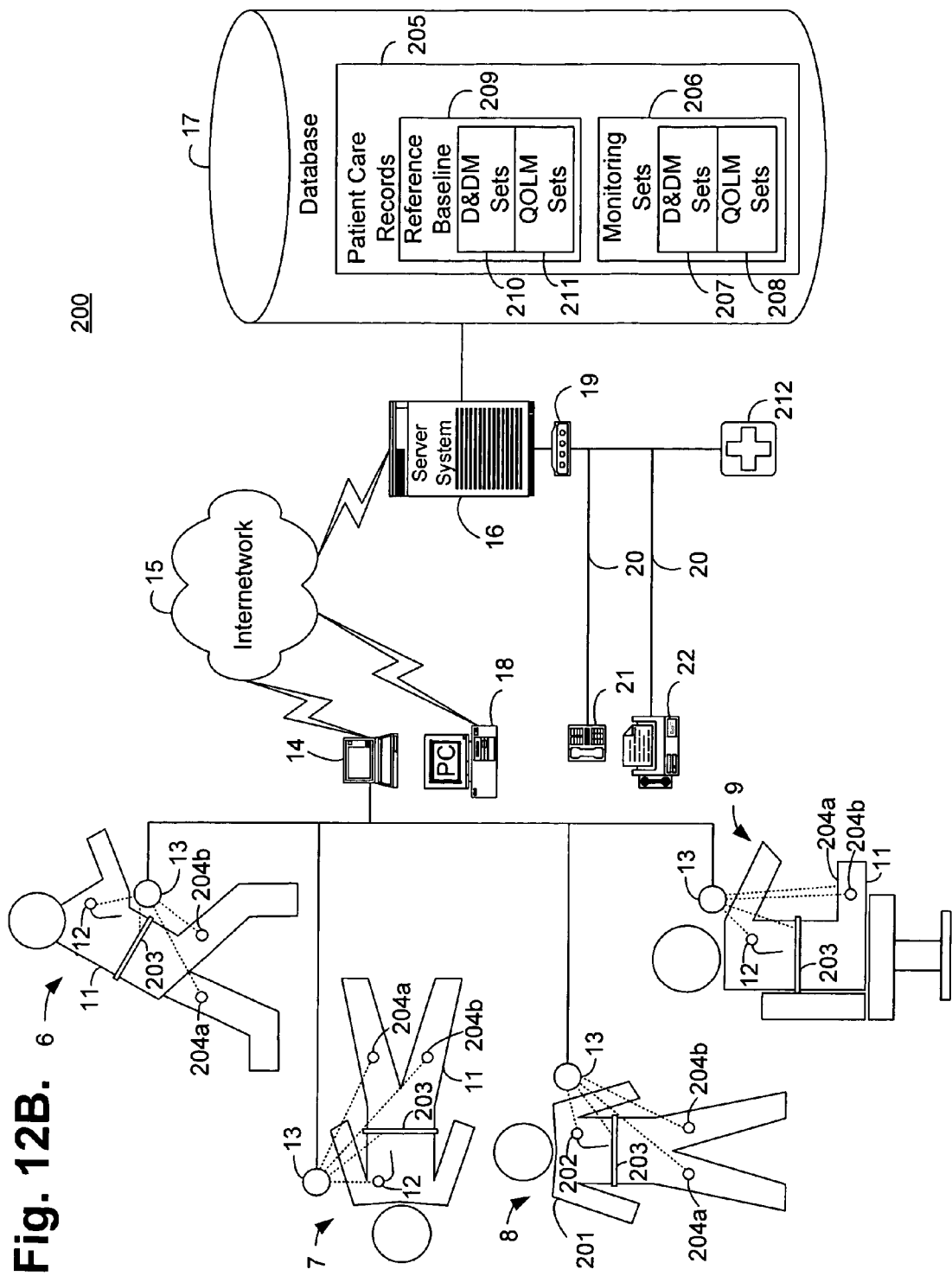

FIGS. 12A and 12B are block diagrams showing system for determining a reference baseline of individual patient status for use in an automated collection and analysis patient care system 200 in accordance with a further embodiment of the present invention. The system 200 provides remote patient care in a manner similar to the system 10 of FIG. 1A and 1B, but with additional functionality for diagnosing and monitoring multiple sites within a patient's body using a variety of patient sensors for diagnosing one or more disorder. The patient 201 can be the recipient of an implantable medical device 202, as described above, or have an external medical device 203 attached, such as a Holter monitor-like device for monitoring electrocardiograms. In addition, one or more sites in or around the patient's body can be monitored using multiple sensors 204a, 204b, such as described in U.S. Pat. Nos. 4,987,897; 5,040,536; 5,113,859; and 5,987,352, the disclosures of which are incorporated herein by reference. One automated system and method for collecting and analyzing retrieved patient information suitable for use with the present invention is described in U.S. Pat. No. 6,270,457, the disclosure of which is incorporated herein by reference. Other types of devices with physiological measure sensors, both heterogeneous and homogenous, could be used, either within the same device or working in conjunction with each other, as is known in the art.

As part of the system 200, the database 17 stores patient care records 205 for each individual patient to whom remote patient care is being provided. Each patient care record 205 contains normal patient identification and treatment profile information, as well as medical history, medications taken, height and weight, and other pertinent data (not shown). The patient care records 205 consist primarily of monitoring sets 206 storing device and derived measures (D&DM) sets 207 and quality of life and symptom measures (QOLM) sets 208 recorded and determined thereafter on a regular, continuous basis. The organization of the device and derived measures sets 205 for an exemplary cardiac patient care record is described above with reference to FIG. 5. The organization of the quality of life and symptom measures sets 208 is further described below with reference to FIG. 14.

The patient care records 205 also include a reference baseline 209, similar to the reference baseline 5 described above, which stores an augmented set of device and derived reference measures sets 210 and quality of life and symptom measures sets 211 recorded and determined during the initial observation period. Other forms of database organization are feasible.

Finally, simultaneous notifications can also be delivered to the patient's physician, hospital, or emergency medical services provider 209 using feedback means similar to that used to notify the patient. As described above, the feedback could be by electronic mail or by automated voice mail or facsimile. The feedback can also include normalized voice feedback, such as described in U.S. Pat. No. 6,261,230, the disclosure of which is incorporated herein by reference.

Figure 13:
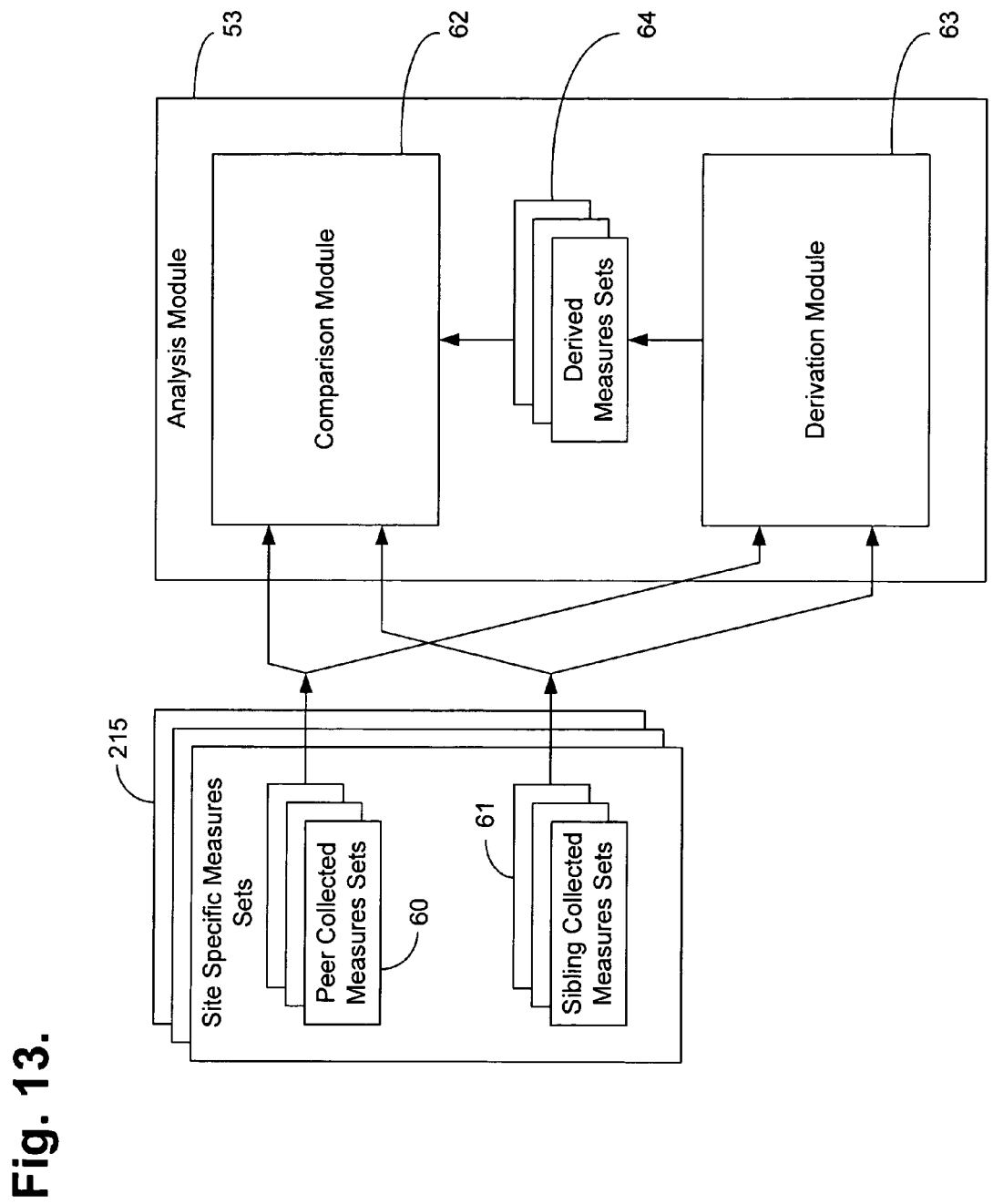
FIG. 13 is a block diagram showing the analysis module of the server system of FIGS. 12A and 12B.

FIG. 13 is a block diagram showing the analysis module 53 of the server system 16 of FIGS. 12A and 12B. The peer collected measures sets 60 and sibling collected measures sets 61 can be organized into site specific groupings based on the sensor from which they originate, that is, implantable medical device 202, external medical device 203, or multiple sensors 204a, 204b. The functionality of the analysis module 53 is augmented to iterate through a plurality of site specific measures sets 215 and one or more disorders.

As described above, as an adjunct to remote patient care through the monitoring of measured physiological data via implantable medical device 202, external medical device 203 and multiple sensors 204a, 204b, quality of life and symptom measures sets 208 can also be stored in the database 17 as part of the monitoring sets 206. A quality of life measure is a semi-quantitative self-assessment of an individual patient's physical and emotional well-being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16.

Figure 14:
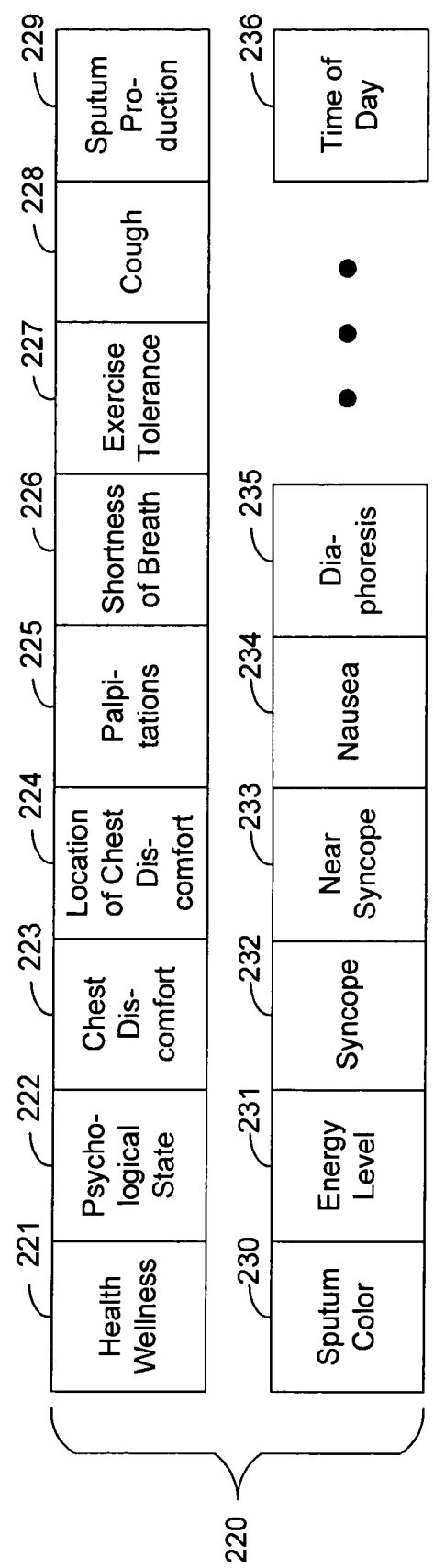
FIG. 14 is a database schema showing, by way of example, the organization of a quality of life and symptom measures set record for care of patients stored as part of a patient care record in the database of the system of FIGS. 12A and 12B.

FIG. 14 is a database schema which augments the database schema described above with reference to FIG. 6 and showing, by way of example, the organization of a quality of life and symptom measures set record 220 for care of patients stored as part of a patient care record 205 in the database 17 of the system 200 of FIGS. 12A and 12B. The following exemplary information is recorded for a patient: overall health wellness 221, psychological state 222, chest discomfort 223, location of chest discomfort 224, palpitations 225, shortness of breath 226, exercise tolerance 227, cough 228, sputum production 229, sputum color 230, energy level 231, syncope 232, near syncope 233, nausea 234, diaphoresis 235, time of day 91, and other quality of life and symptom measures as would be known to one skilled in the art.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452-454, W. B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, also described in Ibid.

The patient may also add non-device quantitative measures, such as the six-minute walk distance, as complementary data to the device and derived measures sets 207 and the symptoms during the six-minute walk to quality of life and symptom measures sets 208.

Figure 15:
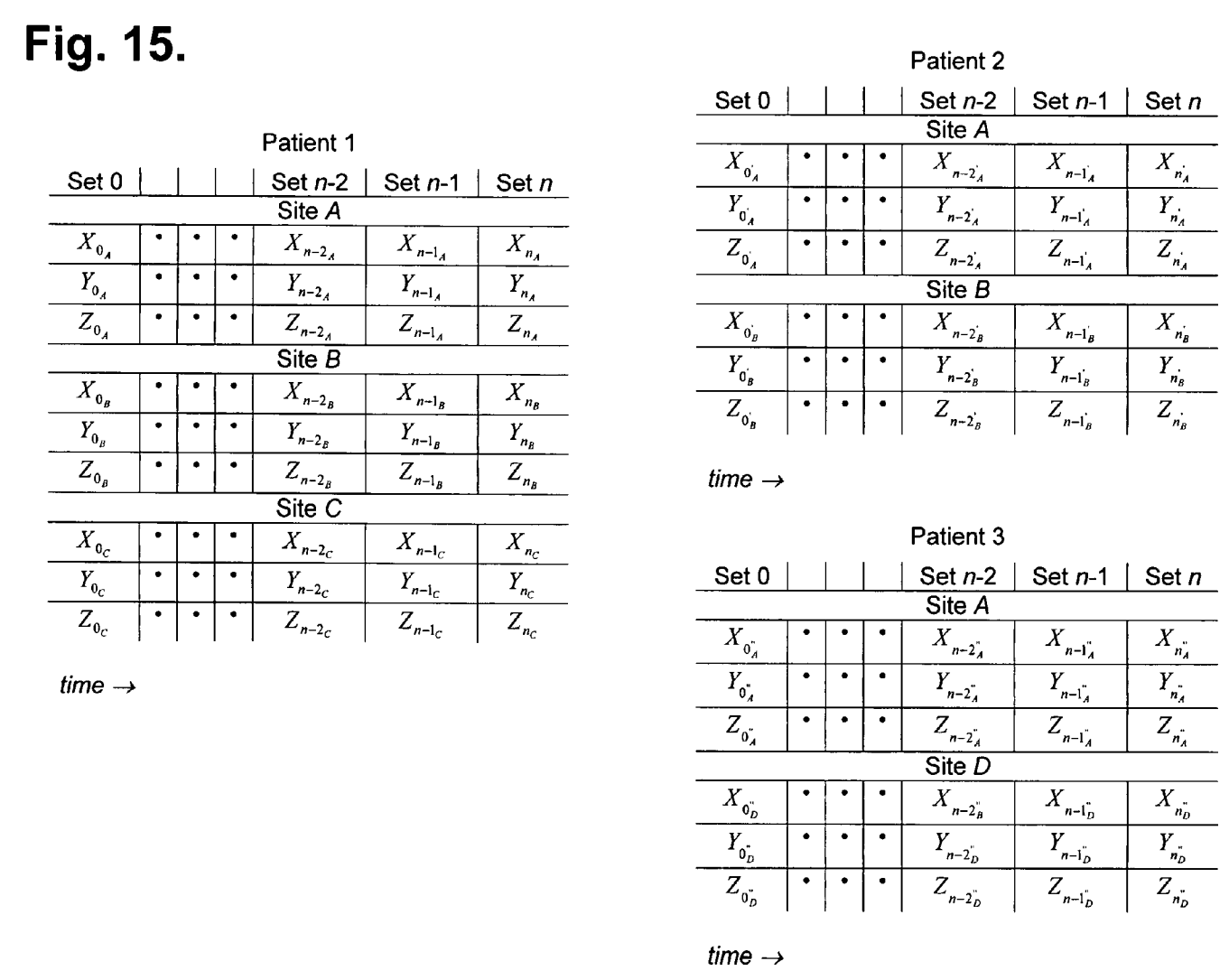

FIG. 15 is a record view showing, by way of example, a set of partial cardiac patient care records stored in the database 17 of the system 200 of FIGS. 12A and 12B. Three patient care records are again shown for Patient 1, Patient 2, and Patient 3 with each of these records containing site specific measures sets 215, grouped as follows. First, the patient care record for Patient 1 includes three site specific measures sets A, B and C, corresponding to three sites on Patient 1's body. Similarly, the patient care record for Patient 2 includes two site specific measures sets A and B, corresponding to two sites, both of which are in the same relative positions on Patient 2's body as the sites for Patient 1. Finally, the patient care record for Patient 3 includes two site specific measures sets A and D, also corresponding to two medical device sensors, only one of which, Site A, is in the same relative position as Site A for Patient 1 and Patient 2.

The analysis module 53 (shown in FIG. 13) performs two further forms of comparison in addition to comparing the individual measures for a given patient to other individual measures for that same patient or to other individual measures for a group of other patients sharing the same disease-specific characteristics or to the patient population in general. First, the individual measures corresponding to each body site for an individual patient can be compared to other individual measures for that same patient, a peer group or a general patient population. Again, these comparisons might be peer-to-peer measures projected over time, for instance, comparing measures for each site, A, B and C, for Patient 1, $X_{n_A}, X_{n'_A}, X_{n''_A}, X_{n-1_A}, X_{n-1'_A}, X_{n-1''_A}, X_{n-2_A}, X_{n-2'_A}, X_{n-2''_A} \ldots X_{0_A}, X_{0'_A}, X_{0''_A}$; $X_{n_B}, X_{n'_B}, X_{n''_B}, X_{n-1_B}, X_{n-1'_B}, X_{n-1''_B}, X_{n-2_B}, X_{n-2'_B}, X_{n-2''_B} \ldots X_{0_B}, X_{0'_B}, X_{0''_B}$; $X_{n_C}, X_{n'_C}, X_{n''_C}, X_{n-1_C}, X_{n-1'_C}, X_{n-1''_C}, X_{n-2_C}, X_{n-2'_C}, X_{n-2''_C} \ldots X_{0_C}, X_{0'_C}, X_{0''_C}$; comparing comparable measures for Site A for the three patients, $X_{n_A}, X_{n'_A}, X_{n''_A}, X_{n-1_A}, X_{n-1'_A}, X_{n-1''_A}, X_{n-2_A}, X_{n-2'_A}, X_{n-2''_A} \ldots X_{0_A}, X_{0'_A}, X_{0''_A}$; or comparing the individual patient's measures to an average from the group. Similarly, these comparisons might be sibling-to-sibling measures for single snapshots, for instance, comparing comparable measures for Site A for the three patients, $X_{n_A}, X_{n'_A}, X_{n''_A}, Y_{n_A}, Y_{n'_A}, Y_{n''_A}$, and $Z_{n_A}, Z_{n'_A}, Z_{n''_A}$, or comparing those same comparable measures for Site A projected over time, for instance $X_{n_A}, X_{n'_A}, X_{n''_A}, Y_{n_A}, Y_{n'_A}, Y_{n''_A}, Z_{n_A}, Z_{n'_A}, Z_{n''_A}, X_{n-1_A}, X_{n-1'_A}, X_{n-1''_A}, Y_{n-1_A}, Y_{n-1'_A}, Y_{n-1''_A}, Z_{n-1_A}, Z_{n-1'_A}, Z_{n-1''_A}, X_{n-2_A}, X_{n-2'_A}, X_{n-2''_A}, Y_{n-2_A}, Y_{n-2'_A}, Y_{n-2''_A}, Z_{n-2_A}, Z_{n-2'_A}, Z_{n-2''_A} \ldots X_{0_A}, X_{0'_A}, X_{0''_A}, Y_{0_A}, Y_{0'_A}, Y_{0''_A}$, and $Z_{0_A}, Z_{0'_A}, Z_{0''_A}$.

Other forms of site-specific comparisons, including comparisons between individual measures from non-comparable sites between patients, are feasible.

Second, the individual measures can be compared on a disorder specific basis. The individual measures stored in each cardiac patient record can be logically grouped into measures relating to specific disorders and diseases, for instance, congestive heart failure, myocardial infarction, respiratory distress, and atrial fibrillation. The foregoing comparison operations performed by the analysis module 53 are further described below with reference to FIGS. 17A-17D.

Figure 16:
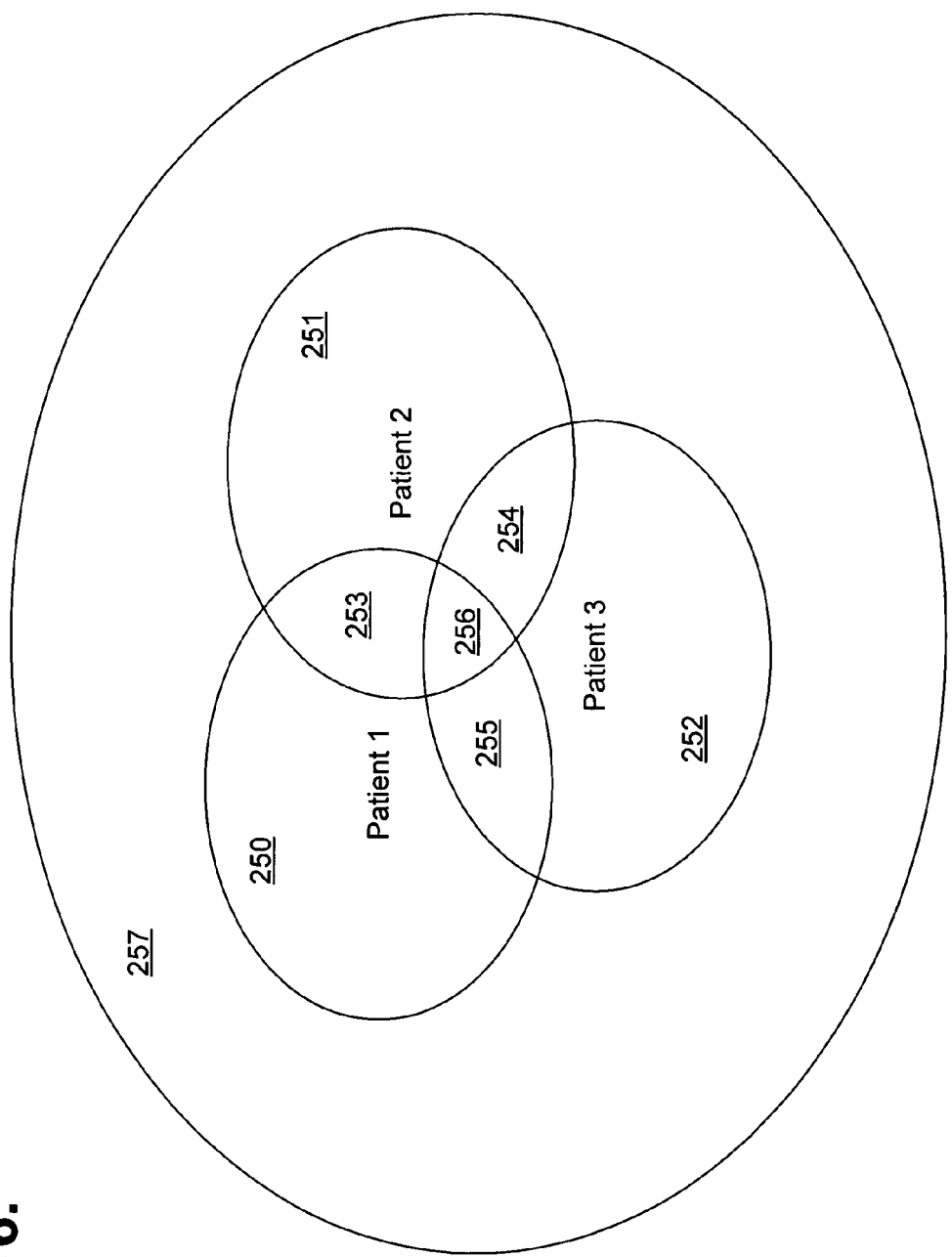
FIG. 16 is a Venn diagram showing, by way of example, peer group overlap between the partial patient care records of FIG. 15.
Figure 17A:
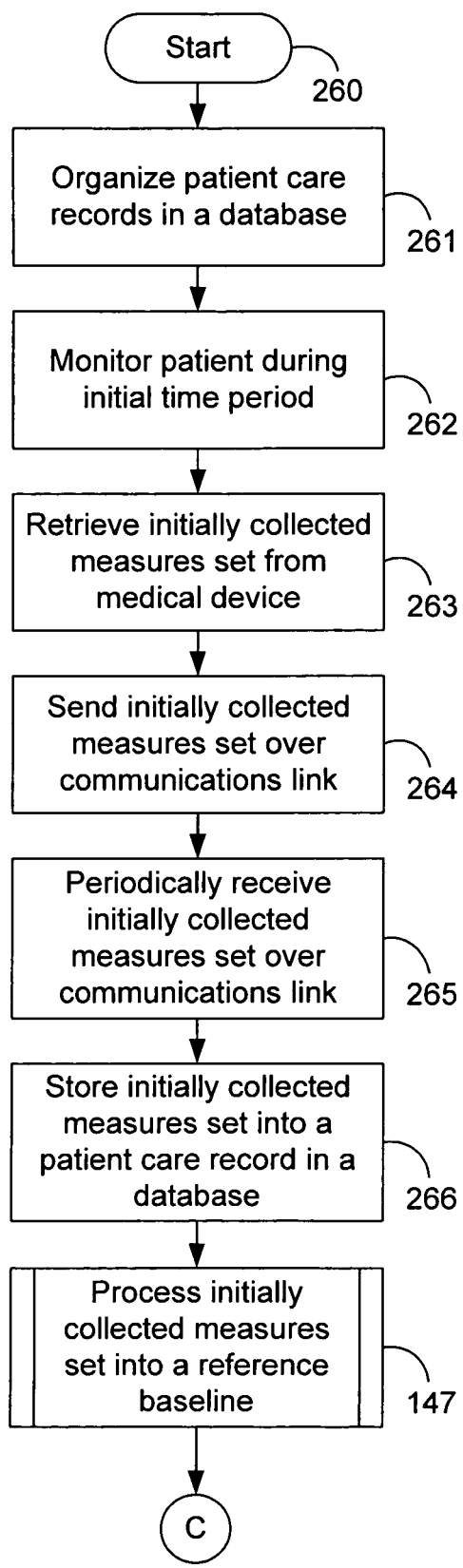
FIGS. 17A- 17D are flow diagrams showing a method for determining a reference baseline of individual patient status for use in an automated collection and analysis patient care system in accordance with a further embodiment of the present invention.
Figure 17B:
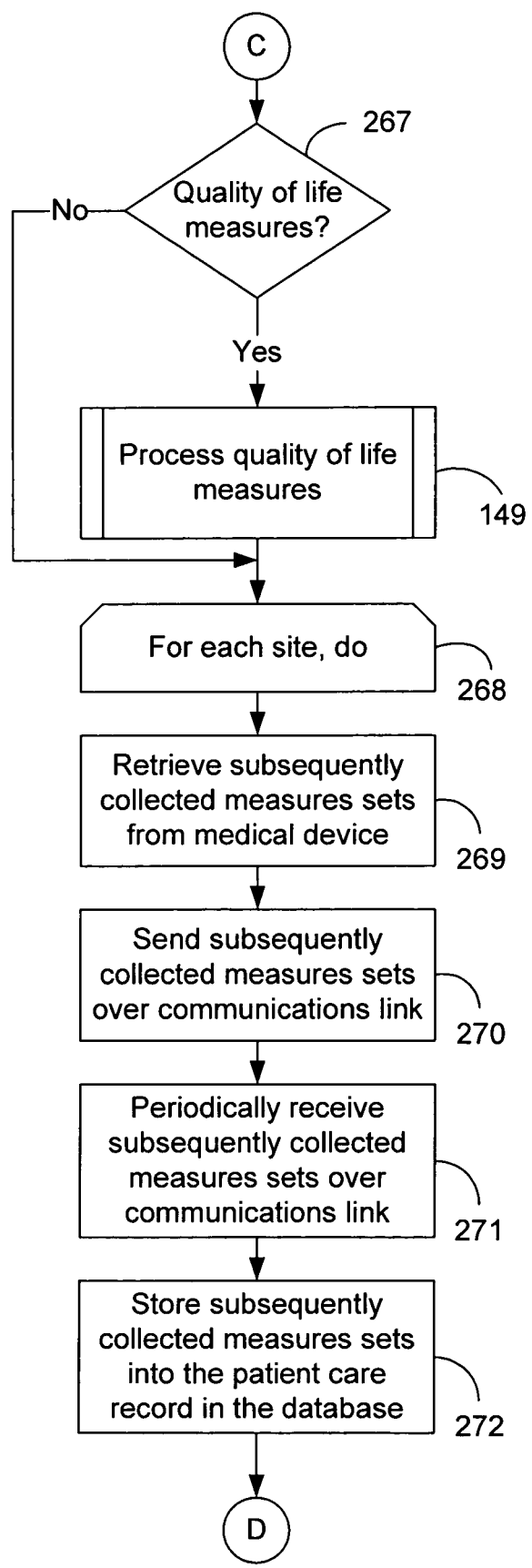
Figure 17C:
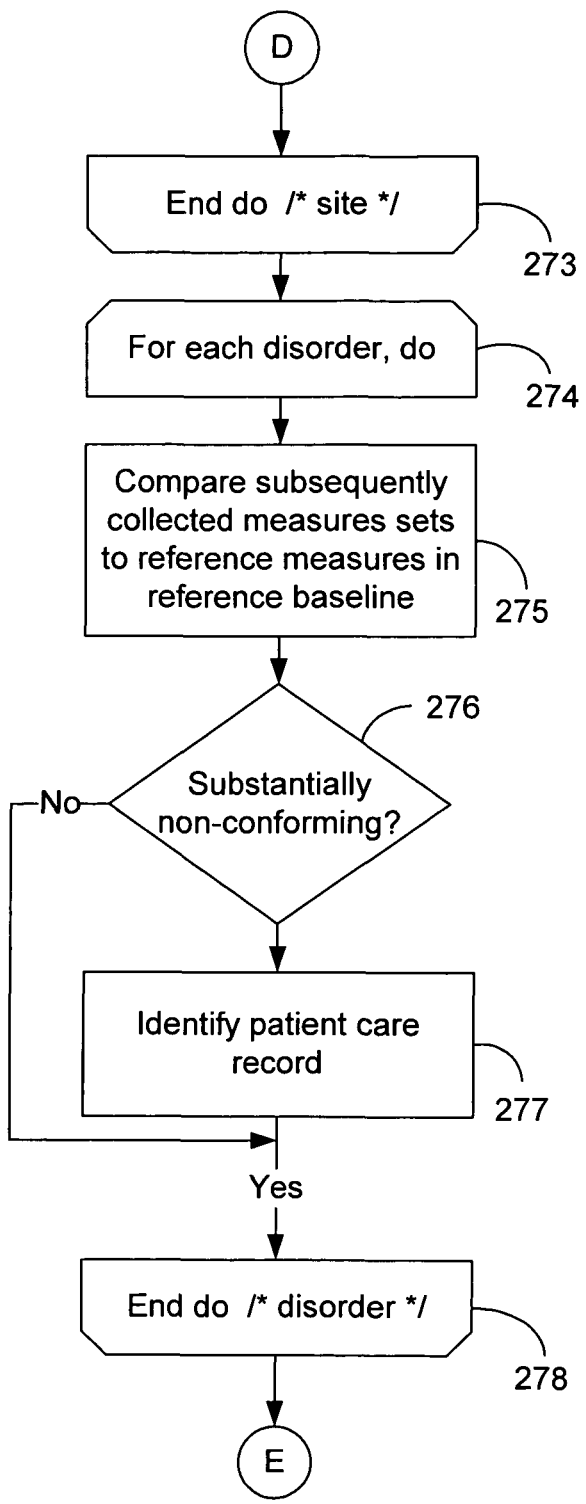
Figure 17D:
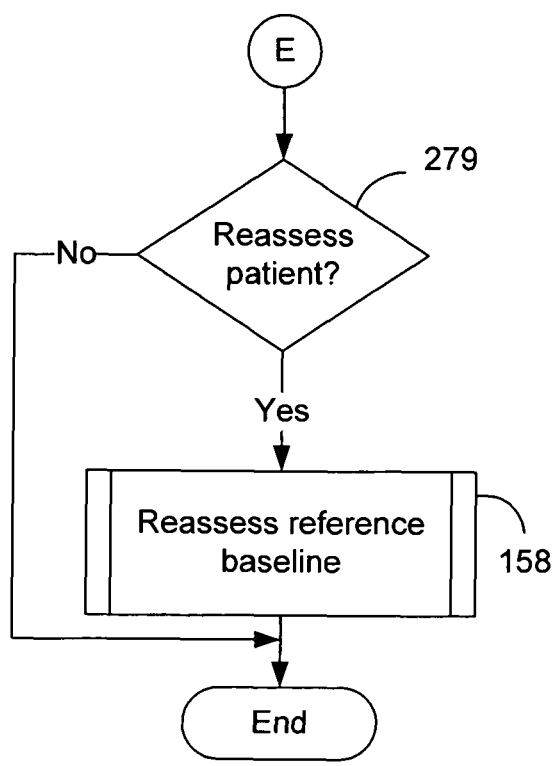

FIG. 16 is a Venn diagram showing, by way of example, peer group overlap between the partial patient care records 205 of FIG. 15. Each patient care record 205 includes characteristics data 250, 251, 252, including personal traits, demographics, medical history, and related personal data, for patients 1, 2 and 3, respectively. For example, the characteristics data 250 for patient 1 might include personal traits which include gender and age, such as male and an age between 40-45; a demographic of resident of New York City; and a medical history consisting of anterior myocardial infraction, congestive heart failure and diabetes. Similarly, the characteristics data 251 for patient 2 might include identical personal traits, thereby resulting in partial overlap 253 of characteristics data 250 and 251. Similar characteristics overlap 254, 255, 256 can exist between each respective patient. The overall patient population 257 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 256 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored.

FIGS. 17A-17D are flow diagrams showing a method for determining a reference baseline of individual patient status for use in an automated collection and analysis patient care system 260 in accordance with a further embodiment of the present invention. As with the method 140 of FIGS. 8A-8C, this method is also implemented as a conventional computer program and performs the same set of steps as described with reference to FIGS. 8A-8C with the following additional functionality. As before, the method 260 operates in two phases: collection and processing of an initial reference baseline 209 (blocks 261-149) and monitoring using the reference baseline 209 (blocks 268-158). Thus, the patient care records are organized in the database 17 with a unique patient care record assigned to each individual patient (block 261).

Next, the reference baseline 209 is determined, as follows. First, the implantable medical device 202, external medical device 203, or the multiple sensors 204a, 204b record the initially collected device measures set 57 during the initial observation period (block 262), as described above with reference to FIG. 5. The initially collected device measures set 57 is retrieved from the medical device (block 263) and sent over the internetwork 15 or similar communications link (block 264) and periodically received by the server system 16 (block 265). The initially collected device measures set 57 is stored into a patient care record in the database 17 for the individual patient 11 (block 266) and processed into the reference baseline 209 (block 147) which stores a reference measures set 59, as described above with reference to FIG. 9. If the quality of life and symptom measures sets 211 are included as part of the reference baseline 209 (block 267), the quality of life and symptom measures sets 211 are processed (block 149), as described above with reference to FIG. 10. Otherwise, the processing of quality of life and symptom measures is skipped (block 267).

Monitoring using the reference baseline 209 involves two iterative processing loops. The individual measures for each site are iteratively obtained in the first processing loop (blocks 268-273) and each disorder is iteratively analyzed in the second processing loop (blocks 274-278). Other forms of flow control are feasible, including recursive processing.

During each iteration of the first processing loop (blocks 268-273), the subsequently collected measures sets for an individual patient are retrieved from the medical device or sensor located at the current site (block 269) using a programmer, interrogator, telemetered signals transceiver, and the like. The retrieved collected measures sets are sent, on a substantially regular basis, over the internetwork 15 or similar communications link (block 270) and periodically received by the server system 16 (block 271). The collected measures sets are stored into the patient care record 205 in the database 17 for that individual patient (block 272).

During each iteration of the second processing loop (blocks 274-278), each of the subsequently collected device measures sets 58 are compared to the reference measures in the reference baseline 209 (block 275). If the subsequently collected device measures sets 58 are substantially non-conforming (block 276), the patient care record is identified (block 277). Otherwise, monitoring continues as before for each disorder. In addition, the measures sets can be further evaluated and matched to diagnose specific medical disorders, such as congestive heart failure, myocardial infarction, respiratory distress, and atrial fibrillation, as described in U.S. Pat. Nos. 6,336,903; 6,368,284; 6,398,728; and 6,411,840, the disclosures of which are incorporated herein by reference. In addition, multiple near-simultaneous disorders can be ordered and prioritized as part of the patient status indicator as described in U.S. Pat. No. 6,440,066, the disclosure of which is incorporated herein by reference.

Finally, if the time for a periodic reassessment has arrived or the subsequently collected device measures sets 58 are substantially non-conforming (block 279), the reference baseline 209 is reassessed (block 158) and a new reference baseline 209 determined, as described above with reference to FIG. 11.

The determination of a reference baseline consisting of reference measures makes possible improved and more accurate treatment methodologies based on an algorithmic analysis of the subsequently collected data sets. Each successive introduction of a new collected device measures set into the database server would help to continually improve the accuracy and effectiveness of the algorithms used.

While the invention has been particularly shown and described as referenced to the embodiments thereof, those skilled in the art will understand that the foregoing and other changes in form and detail may be made therein without departing from the spirit and scope of the invention.

What is claimed is:

1. An apparatus for automated patient management, comprising:
    an identification module to receive information comprising treatment profile and medical history to identify a patient for enrollment in automated patient management;
    a collected measures module to receive collected device measures as raw physiometry for the patient regularly recorded by a medical device, beginning with an initial observation period;
    a derived measures module to receive derived device measures as derivative physiometry based on the collected device measures;
    a quality of life module to receive quality of life measures over the initial observation period contemporaneous to recordation of the collected device measures, wherein the quality of life measures provide a self-assessment of physical and emotional well-being by the patient;
    a processing module to process the collected and derived device measures and the quality of life measures into a reference baseline comprising a set of reference measures;
    an acceptance module to receive acceptance parameters as a threshold for the reference measures in the reference baseline to determine automated patient care eligibility, wherein the acceptance parameters are indicator values consistent with the presence of some form of chronic yet stable disease, which does not require immediate emergency care; and
    a processor to execute the modules.

2. An apparatus according to claim 1, further comprising:
    a determination module to determine a wellness indicator by analyzing one or more of the collected and derived device measures against the acceptance parameters.

3. An apparatus according to claim 1, further comprising:
    a non-acceptance module to receive non-acceptance parameters as a threshold for the reference measures in the reference baseline in terms of one or more of substantially normal activity and exercise; and
    a determination module to determine a rejection indicator by analyzing one or more of the collected and derived device measures against the non-acceptance parameters.

4. An apparatus according to claim 1, wherein a set of timed physical stressors are performed by the patient over the initial observation period contemporaneous to recordation of the collected device measures.

5. An apparatus according to claim 1, further comprising:
    a reprogramming module to define reprogramming parameters for the medical device, wherein the collected device measures are recorded subsequent to application of the reprogramming parameters.

6. A system for providing baseline data for automated patient management, comprising:
    a database, comprising:
        information to identify a patient for enrollment in automated patient management and comprising treatment profile and medical history;
        collected device measures to provide raw physiometry for the patient regularly recorded by a medical device, beginning with an initial observation period;
        derived device measures based on the collected device measures to provide derivative physiometry; and
        quality of life measures to provide data electronically recorded over the initial observation period contemporaneous to recordation of the collected device measures, wherein the quality of life measures provide a self-assessment of physical and emotional well-being by the patient;
    an interface module to periodically receive the collected device measures from the medical device;
    an application module to derive the derived device measures from the collected device measures;
    a processing module to process the collected and derived device measures and the quality of life measures into a reference baseline comprising a set of reference measures;
    an acceptance module to receive acceptance parameters as a threshold for the reference measures in the reference baseline to determine automated patient care eligibility, wherein the acceptance parameters are indicator values consistent with the presence of some form of chronic yet stable disease, which does not require immediate emergency care; and
    a processor to execute the modules.

7. A system according to claim 6, further comprising:
    a determination module to determine a wellness indicator by analyzing one or more of the collected and derived device measures against the acceptance parameters.

8. A system according to claim 6, further comprising:
    a non-acceptance module to receive non-acceptance parameters to define a threshold for the reference measures in the reference baseline in terms of one or more of substantially normal activity and exercise; and
    a determination module to determine a rejection indicator by analyzing one or more of the collected and derived device measures against the non-acceptance parameters.

9. A system according to claim 6, wherein a set of timed physical stressors are performed by the patient over the initial observation period contemporaneous to recordation of the collected device measures.

10. A system according to claim 6, further comprising:
    a reprogramming module to define reprogramming parameters for the medical device, wherein the collected device measures are recorded subsequent to application of the reprogramming parameters.

11. A system according to claim 6, wherein the medical device is selected from the set comprising an implantable medical device and an external medical device.

12. A system for automated patient management, comprising:
a data collection module to receive device data for a patient for enrollment in automated patient management, comprising at least one of:
an identification module to receive information to identify the patient comprising treatment profile and medical history;
a collected measures module to receive collected device measures as raw physiometry for the patient regularly recorded by a medical device, beginning with an initial observation period; and
a derived measures module to receive derived device measures as derivative physiometry based on the collected device measures; and
a quality of life module to receive quality of life measures over the initial observation period contemporaneous to recordation of the collected device measures, wherein the quality of life measures provide a self-assessment of physical and emotional well-being by the patient; and
a processing module to process the collected and derived device measures and the quality of life measures into a reference baseline comprising a set of reference measures;
an analysis module to determine a wellness indicator by analyzing one or more of the collected and derived device measures against acceptance parameters that define a threshold for one or more of the reference measures in the reference baseline to determine automated patient care eligibility, wherein the acceptance parameters are indicator values consistent with the presence of some form of chronic yet stable disease, which does not require immediate emergency care; and
a processor to execute the modules.

13. A system according to claim 12, further comprising:
a reprogramming module to define reprogramming parameters for the medical device, wherein the collected device measures are recorded subsequent to application of the reprogramming parameters.

* * * * *